United States Patent
Sivik et al.

(10) Patent No.: US 6,844,309 B1
(45) Date of Patent: Jan. 18, 2005

(54) ETHER-CAPPED POLY(OXYALKYLATED) ALCOHOL SURFACTANTS

(75) Inventors: Mark Robert Sivik, Deerfield Township, OH (US); Glenn Thomas Jordan, IV, Indian Springs, OH (US); Bernard William Kluesener, Harrison, OH (US); William Michael Scheper, Lawrenceburg, IN (US); Donna Jean Haeggberg, Cincinnati, OH (US); Kristen Lynne McKenzie, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 414 days.

(21) Appl. No.: 09/660,175

(22) Filed: Sep. 12, 2000

Related U.S. Application Data

(60) Provisional application No. 60/169,569, filed on Dec. 8, 1999, and provisional application No. 60/169,706, filed on Dec. 8, 1999.

(51) Int. Cl.[7] .......................... C11D 1/72; C11D 1/722; C11D 3/37
(52) U.S. Cl. ...................... 510/475; 510/356; 510/360; 510/421; 510/524; 510/535
(58) Field of Search ............................... 510/356, 360, 510/421, 475, 524, 535

(56) References Cited

U.S. PATENT DOCUMENTS

| | | |
|---|---|---|
| 3,082,172 A | 3/1963 | Temple et al. |
| 3,255,117 A | 6/1966 | Knapp et al. |
| 3,281,475 A | 10/1966 | Boettner et al. |
| 4,272,394 A | 6/1981 | Kaneko |
| 4,317,940 A | 3/1982 | Scardera et al. |
| 4,827,028 A | 5/1989 | Scardera et al. |
| 4,898,621 A | 2/1990 | Pruehs et al. |
| 4,902,834 A | 2/1990 | Otten et al. |
| 4,913,833 A | 4/1990 | Otten et al. |
| 4,925,587 A | 5/1990 | Schenker et al. |
| 5,073,286 A | 12/1991 | Otten et al. |
| 5,206,443 A | 4/1993 | Baur et al. |
| 5,294,365 A | 3/1994 | Welch et al. |
| 5,346,973 A | 9/1994 | Feustel et al. |
| 5,425,894 A | 6/1995 | Welch et al. |
| 5,576,281 A | 11/1996 | Bunch et al. |
| 5,677,273 A | 10/1997 | Schmid et al. |
| 5,921,910 A | 7/1999 | Schmid et al. |
| 6,593,287 B1 * | 7/2003 | Jordan et al. ................ 510/475 |

FOREIGN PATENT DOCUMENTS

| | | | | |
|---|---|---|---|---|
| DE | 2252186 A | 5/1974 | | |
| DE | 2556544 A | 6/1977 | | |
| DE | 2556544 | * 6/1977 | | ............ C11D/1/72 |
| DE | 0337760 A | 10/1989 | | |
| EP | 0638635 A1 | 2/1995 | | |
| EP | 0675942 B1 | 7/1997 | | |
| GB | 2158080 A | 11/1985 | | |
| GB | 2158080 | * 11/1985 | | ........... C08G/65/32 |
| WO | WO 93/04153 A1 | 3/1993 | | |
| WO | WO 94/22800 A1 | 10/1994 | | |
| WO | WO 95/13260 A1 | 5/1995 | | |
| WO | WO 96/00253 A | 1/1996 | | |
| WO | WO 96/12001 A1 | 4/1996 | | |
| WO | WO 98/17379 A1 | 4/1998 | | |
| WO | WO 99/06466 A1 | 2/1999 | | |

* cited by examiner

*Primary Examiner*—Brian P. Mruk
(74) *Attorney, Agent, or Firm*—Laura R. Grunzinger; Ian S. Robinson; Kim William Zerby

(57) ABSTRACT

Ether-capped poly(oxyalkylated) alcohol surfactants having superior grease cleaning abilities and improved spotting/filming benefits are provided. The alcohol surfactants have the formula:

$$RO(R^1O)_xR^2$$

wherein, R is selected from the group consisting of linear or branched, saturated or unsaturated, substituted or unsubstituted, aliphatic or aromatic hydrocarbon radicals having from about 1 to about 30 carbon atoms; $R^1$ may be the same or different, and is independently selected from the group consisting of branched or linear $C_2$ to $C_7$ alkylene in any given molecule; $R^2$ is selected from the group consisting of:

(i) a 4 to 8 membered substituted, or unsubstituted heterocyclic ring containing from 1 to 3 hetero atoms;

(ii) a 7 to 13 membered substituted, or unsubstituted polycyclic ring;

(iii) a hydrocarbon of the formula:

$$-(CH_2)_y-X$$

wherein, y is an integer from 1 to 7, X is a 4 to 8 membered substituted, or unsubstituted, saturated or unsaturated cyclic or aromatic hydrocarbon radical; and (iv) a hydrocarbon radical of the formula:

$$-C(CH_3)_2R^3$$

wherein $R^3$ is selected from the group consisting of linear or branched, saturated or unsaturated, substituted or unsubstituted, aliphatic or aromatic hydrocarbon radicals having from about 1 to about 30 carbon atoms, provided that when $R^3$ is methyl, R is branched;

wherein x is a number from 1 to about 30.

31 Claims, No Drawings

ETHER-CAPPED POLY(OXYALKYLATED) ALCOHOL SURFACTANTS

This application claims priority to Provisional Application Ser. Nos. 60/169,569, filed Dec. 8, 1999, and 60/169,706, filed Dec. 8, 1999.

TECHNICAL FIELD

The present invention relates to low-foaming nonionic surfactants and more particularly to ether-capped poly (oxyalkylated) alcohol surfactants which have superior spotting and filming benefits in dishwashing and hard surface cleaning applications.

BACKGROUND OF THE INVENTION

Due to the varied nature of different cleaning compositions, different surfactants are better suited for some applications while being less suited or totally unsuitable for other applications. Nonionic surfactants, such as alcohol ethoxylates, alkyl polyglycosides, and alkyl glucose amides are of considerable importance in detergent products. For example, under some conditions, nonionic surfactants aid cleaning of greasy soils and inhibit the formation of calcium soap. However, conventional nonionic surfactants designed for effective cleaning in laundry products form liquid crystalline phases on mixing with water. These phases can hinder the rate of mixing with water and lead to undesirable optical properties of thin films on solution drying. For example, conventional nonionics sprayed on the surface of granules to achieve target density can give rise to poor granule dissolution and residue in horizontal axis machine dispensers. Conventional nonionics formulated at high levels in liquid products can lead to poor rates of mixing with water and consumer concern. Conventional nonionics in window and floor cleaners can form visible liquid crystalline films on drying that increase the effort required by the consumer to achieve good results. Similarly, a nonionic surfactant for use in an automatic dishwashing would need to minimize foam production and not leave undesirable spots and films on the cleaned surfaces.

On account of the foregoing technical constraints as well as consumer needs and demands, product compositions are undergoing continual change and improvement. Moreover environmental factors such as the need for biodegradable materials, the restriction of phosphate, the desirability of providing ever-better cleaning results with less product, providing less thermal energy demand, and less water to assist the washing process, have all driven the need for improved compositions.

Accordingly, the need remains for new surfactants which are suitable for use in a variety of compositions which can provide improve dissolution of solid products (like bars and tablets) and granular products, improved rates of mixing with water as with liquid products, improved streaking and filming performance as in hard surface cleaners and automatic dishwashing, good cleaning, suds control and good biodegradability while avoiding incompatibility with other cleaning surfactants and/or bleach.

BACKGROUND ART

U.S. Pat. No. 4,272,394, WO 94/22800, and WO 93/04153.

SUMMARY OF THE INVENTION

This need is met by the present invention wherein a low-foaming nonionic surfactant is provided. The low-foaming nonionic surfactant, either alone or in combination with other surfactants, provides improved spotting and filming performance as well as improved cleaning performance on greasy soils and suds or foam suppression in certain applications. While not wishing to be bound by theory, it is believed the alcohol surfactants of the present invention deliver superior spotting and filming benefits via improved sheeting action. As for improved cleaning performance on greasy soils, such benefits are shown when the alcohol surfactants of the present invention are employed in conjunction with a high cloud point nonionic surfactant as disclosed in detail herein. Lastly, certain alcohol surfactants of the present invention may also act to reduce the suds or foaming associated with food soils or various other cleaning agents.

In accordance with an aspect of the present invention, an ether-capped poly(oxyalkylated) alcohol surfactant is provided. The alcohol has the formula:

$$RO(R^1O)_xR^2$$

wherein, R is selected from the group consisting of linear or branched, saturated or unsaturated, substituted or unsubstituted, aliphatic or aromatic hydrocarbon radicals having from about 1 to about 30 carbon atoms; $R^1$ may be the same or different, and is independently selected from the group consisting of branched or linear $C_2$ to $C_7$ alkylene in any given molecule; $R^2$ is selected from the group consisting of:

(i) a 4 to 8 membered substituted, or unsubstituted heterocyclic ring containing from 1 to 3 hetero atoms;

(ii) a 7 to 13 membered substituted, or unsubstituted polycyclic ring;

(iii) a hydrocarbon of the formula:

$$-(CH_2)_y-X$$

wherein, y is an integer from 1 to 7, X is a 4 to 8 membered substituted, or unsubstituted, saturated or unsaturated cyclic or aromatic hydrocarbon radical; and (iv) a hydrocarbon radical of the formula:

$$-C(CH_3)_2R^3$$

wherein $R^3$ is selected from the group consisting of linear or branched, saturated or unsaturated, substituted or unsubstituted, aliphatic or aromatic hydrocarbon radicals having from about 1 to about 30 carbon atoms, provided that when $R^3$ is methyl, R is branched;

wherein x is a number from 1 to about 30.

These and other aspects, features and advantages will become apparent to those of ordinary skill in the art from a reading of the following detailed description and the appended claims. All percentages, ratios and proportions herein are by weight, unless otherwise specified. All temperatures are in degrees Celsius (°C.) unless otherwise specified. All documents cited are in relevant part, incorporated herein by reference.

DETAILED DESCRIPTION OF THE INVENTION

Once again, the present invention is directed toward a low-foaming nonionic surfactant for use in detergent compositions. The surfactant of the present invention is of the formula:

$$RO(R^1O)_xR^2$$

In one aspect of the present invention R is a linear or branched, saturated or unsaturated, substituted or unsubstituted, aliphatic hydrocarbon radical having from about 1 to about 20 carbon atoms, even more preferably R is a linear or branched, saturated, aliphatic hydrocarbon radicals having from about 4 to about 18 carbon atoms.

In one aspect of the present invention R, $R^1$ and $R^2$ are selected such that the ether-capped poly(oxyalkylated) alcohol surfactant contains one or more chiral carbon atoms.

In one aspect of the present invention, R is a hydrocarbon radical of the formula:

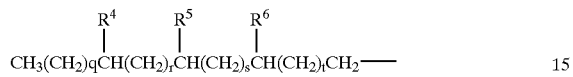

wherein $R^4$, $R^5$, and $R^6$ are each independently selected from hydrogen, and $C_1$–$C_3$ alkyl, more preferably hydrogen, $C_1$–$C_2$ alkyl, even more preferably hydrogen, and methyl, provided that $R^4$, $R^5$, and $R^6$ are not all hydrogen and, when t is 0, at least $R^4$ or $R^5$ is not hydrogen; q, r, s, t are each independently integers from 0 to 13. In one embodiment of this aspect of the present invention R is selected from the formulas:

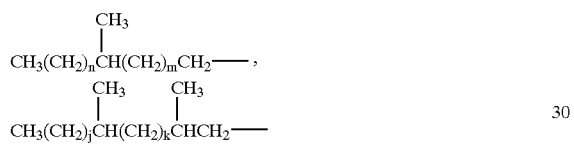

wherein n, m, j and k are each independently integers from 0 to 13.

In one aspect of the present invention $R^2$ is a hydrocarbon radical of the formula:

—C(CH₃)₂R³

$R^3$ is selected from the group consisting of linear or branched, saturated or unsaturated, substituted or unsubstituted, aliphatic or aromatic hydrocarbon radicals having from about 1 to about 30, more preferably 1 to 20, even more preferably 1 to 15, carbon atoms, provided that when $R^3$ is methyl, R is branched. In one embodiment of this aspect of the present invention, $R^3$ is ethyl.

In one aspect of the present invention $R^2$ is a 4 to 8 membered substituted, or unsubstituted heterocyclic ring containing from 1 to 3 hetero atoms. In one embodiment of this aspect of the invention the hetero atoms are selected from the group comprising oxygen, nitrogen, sulfur and mixtures thereof. In one embodiment of this aspect of the invention $R^2$ is a 5 or 6 member heterocycle. In another embodiment of this aspect of the present invention $R^2$ is selected from the group consisting of:

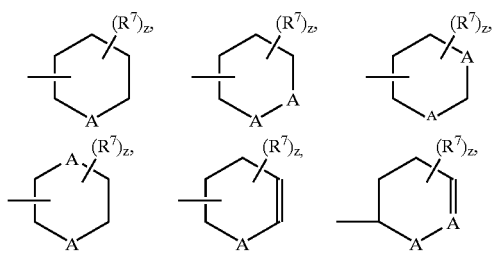

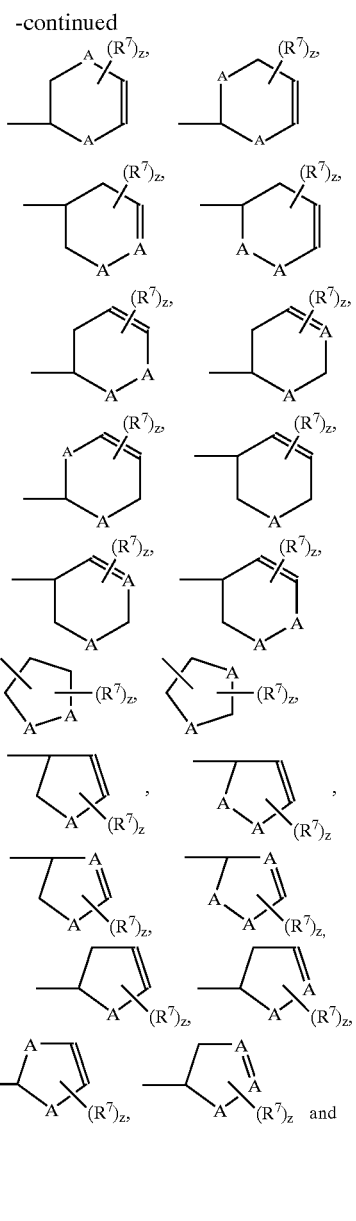

wherein each $R^7$ is independently selected from the group consisting of hydrogen, linear or branched, saturated or unsaturated, substituted or unsubstituted, aliphatic hydrocarbon or alkoxy radical having from about 1 to about 10 carbon atoms, or $R^7$ is a saturated or unsaturated, substituted or unsubstituted, alicyclic or aromatic hydrocarbon radical having, from about 1 to about 10 carbon atoms, which is fused to the heterocyclic ring; each A is independently selected from the group consisting of O, and $N(R^8)_a$, wherein $R^8$ is independently selected from the group consisting of hydrogen, linear or branched, saturated or unsaturated, substituted or unsubstituted, aliphatic hydrocarbon radical having from about 1 to about 10 carbon atoms, and a is either 0 or 1; z is an integer from 1 to 3.

In another embodiment of this aspect of the present invention $R^2$ is selected from the group consisting of:

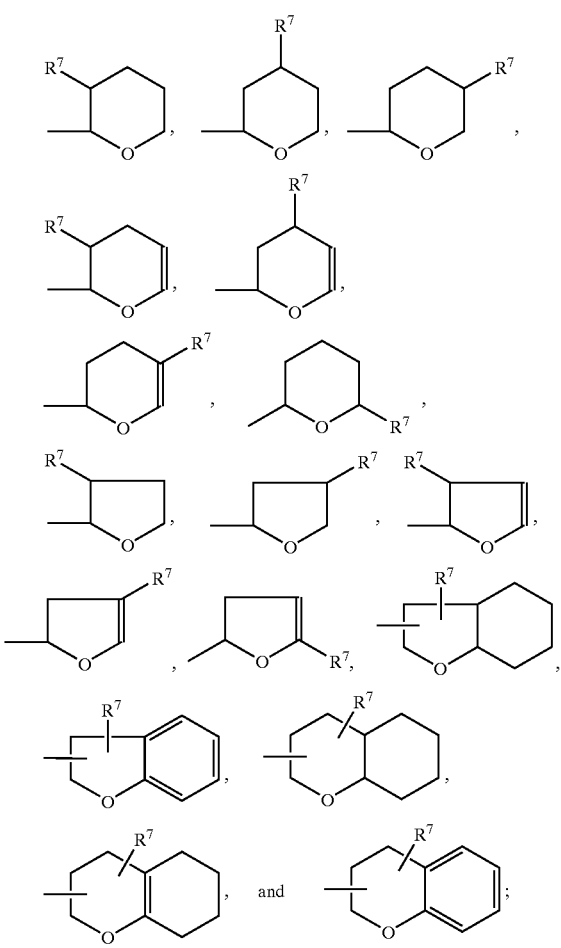

wherein R⁷ is defined as above.

In another embodiment of this aspect of the present invention R² is selected from the group consisting of:

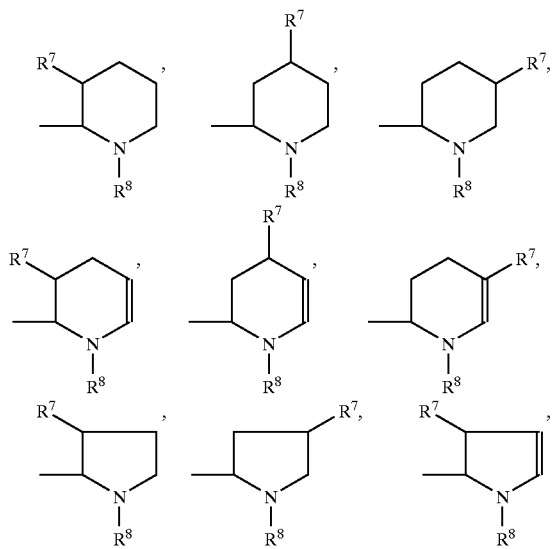

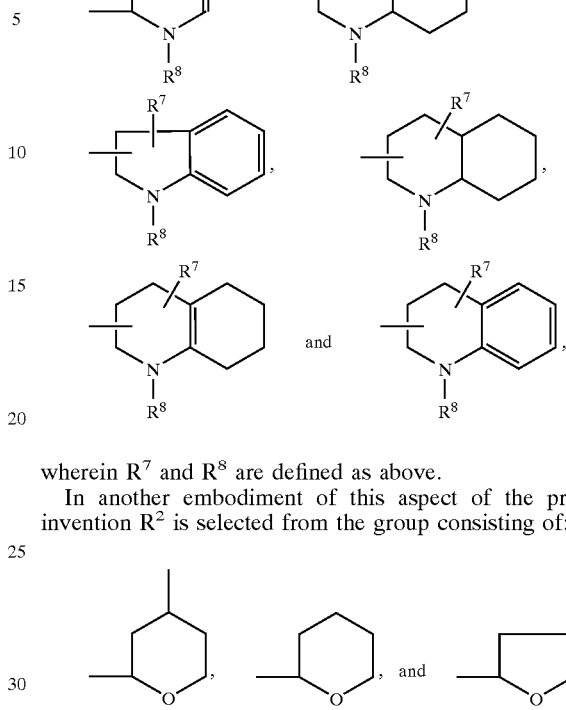

wherein R⁷ and R⁸ are defined as above.

In another embodiment of this aspect of the present invention R² is selected from the group consisting of:

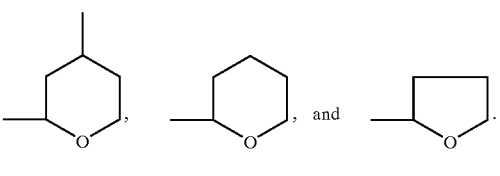

In another embodiment of this aspect of the present invention R² is selected from the group consisting of:

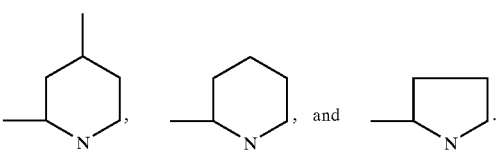

In one aspect of the present invention R² is a 7 to 13 membered substituted, or unsubstituted polycyclic ring. In one embodiment of this aspect of the present invention R² is selected from the group consisting of substituted, or unsubstituted adamantane, substituted, or unsubstituted norbornane, substituted, or unsubstituted nortricyclene, and substituted, or unsubstituted bicyclo[2.2.2]octane. In another embodiment of this aspect of the present invention R² is a substituted, or unsubstituted adamantane.

In one aspect of the present invention R² is a hydrocarbon of the formula:

—(CH₂)<sub>y</sub>—X wherein, y is an integer from 1 to 7, X is a 4 to 8 membered substituted, or unsubstituted, saturated or unsaturated cyclic or aromatic hydrocarbon radical. In another embodiment of this aspect of the present invention y is an integer from 1 to 2, and X is selected from the group consisting of to 5 to 8 membered substituted, or unsubstituted, aromatic hydrocarbon radical.

In another embodiment of this aspect of the present invention y is 0 and X is a 5 or 6 membered substituted, or unsubstituted, saturated or unsaturated cyclic or aromatic hydrocarbon radical.

In another embodiment of this aspect of the present invention X is selected from the group consisting of:

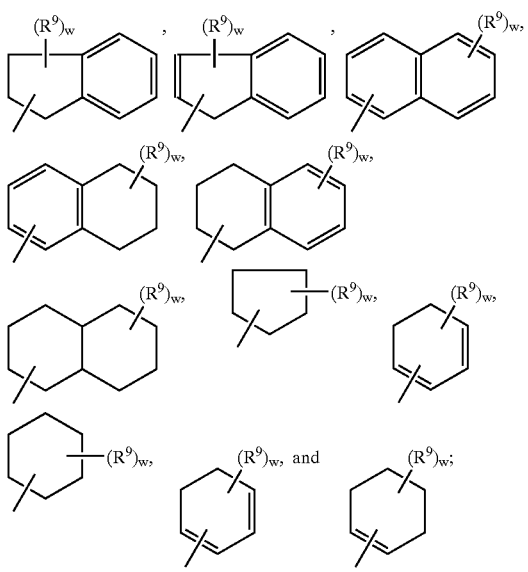

wherein each $R^9$ is independently selected from the group consisting of hydrogen, linear or branched, saturated or unsaturated, substituted or unsubstituted, aliphatic hydrocarbon or alkoxy radical having from about 1 to about 10 carbon atoms, or $R^9$ is a saturated or unsaturated, substituted or unsubstituted, alicyclic or aromatic hydrocarbon radical having, from about 1 to about 10 carbon atoms, which is fused to the ring; w is an integer from 1 to 3.

In another embodiment of this aspect of the present invention X is selected from the group consisting of:

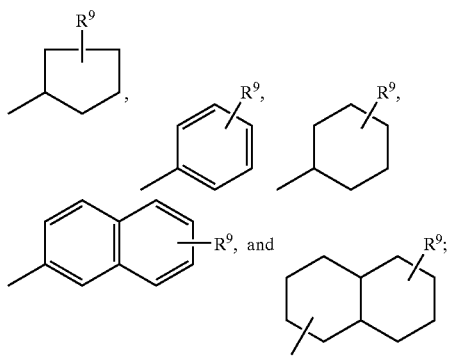

wherein $R^9$ is defined as above.

In another embodiment of this aspect of the present invention X is selected from the group consisting of:

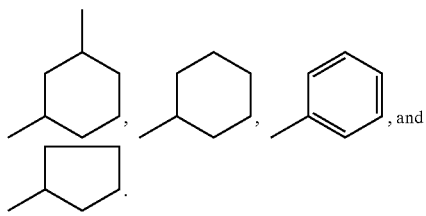

In one aspect of the present invention, when x is greater than 2, $R^1$ may be the same or different. That is, $R^1$ may vary between any of the branched or linear $C_2$ to $C_7$ alkylene units as described above. For instance, if x is 3, $R^1$ may be selected to form ethlyeneoxy(EO) or propyleneoxy(PO) and may vary in order of (EO)(PO)(EO), (EO)(EO)(PO); (EO)(EO)(EO); (PO)(EO)(PO); (PO)(PO)(EO) and (PO)(PO)(PO). Of course, the integer three is chosen for example only and the variation may be much larger with a higher integer value for x and include, for example, multiple (EO) units and a much small number of (PO) units. Similarly, ethylene, and propylene chosen for example only and the variation may be much larger with selection of linear or branched butylene, pentylene, hexylene and/or heptylene.

The surfactants of the present invention can be prepared via a variety of different process. In one aspect of the present invention, when $R^2$ is other than a heterocycle, the surfactants may be prepared by reacting an alcohol formula:

$R^2OH$ wherein $R^2$ is as defined above, but is other than a heterocycle; with an alkoxylated alcohol of the formula $RO(R^1O)_xH$ wherein R, $R^1$, and x, are as defined above, in the presence of a catalyst to form the ether-capped poly(oxyalkylated) alcohol.

In one embodiment of this aspect of the present invention the step of reacting the alcohol with the alkoxylated alcohol is conducted in the presence of a catalyst. Suitable catalysts include Lewis acids; acids; polymers; clays, such as, Spanish sepiolite clay, GIRDLER K-10; zeolites, such as HZS-360 zeolite, H-Y zeolite; sulfonated charcoal; and mixtures thereof.

Suitable Lewis acids include, but are not limited to, $TiCl_4$, $Ti(O^iPr)_4$, $ZnCl_2$, $SnCl_2$, $AlCl_3$, platinum dichloride, copper (II) chloride, phosphorous pentachloride, phosphorous trichloride, cobalt(II) chloride, zinc oxide, iron(II) chloride and $BF_3$—$OEt_2$.

Suitable inorganic acids and their salts include, mineral acids, such as, phosphoric acid, sulfuric acid, hydrochloric acid, phosphorous oxychloride. Furthermore, the mineral acids or their salts can optionally be adsorbed on to a substrate, such as, silica gel, or alumina. For example sulfuric acid adsorbed on silica gel, or alumina impregnated with zinc chloride.

Suitable organic acids and their salts include: halogenated carboxylic acids, such as, trifluoroacetic acid, heptaflurobutyric acid, dichloroacetic acid, and trichloroacetic acid; and sulfonic and sulfinic acids and their salts such as, p-toluenesulfonic acid, p-toluenesulfinic acid, methanesulfonic acid, 4-bromobenzene sulfonic acid, naphthalenesulfonic acid, (±)-10-camphorsulfonic acid and isomers, and alkyl benzenesulfonic acid, xylenesulfonic acid and cumenesulfonic acid.

Suitable polymers, include, but are not limited to, polymeric ion exchange resins. Suitable polymeric ion exchange resins include those of the Amberylst series, such as AMBERYLST® 15, available from Rohm & Haas, the DOWEX® series, such as, DOWEX 50X8-50 available from Dow; REILLEX 424, available from Reilly Industries; the Amberlite series, such as AMBERLITE IRA-400, or AMBERLITE IR-118, available from Rohm & Haas; available from United Catalyst; the ENVIROCAT series, such as ENVIROCAT EPZG, available from Contract Chemicals; and combinations thereof.

Other suitable catalysts include, mercury(II) trifluroacetate, alkylether sulfuric acids, alkyl sulfuric acids, triflurormethanesulfonic acid (triflic acid) and anhydride, sulfonated cationic exchange resin, formed ionite catalyst, phosphoric acid tungsten complex, polysorb 1, cerium(III)

chloride, fluorophosphoric acid, chromium (Cr3+), HF modified clay, triflic acid modified clay, perchloric acid, potassium hydrogensulfate, hexamethyltriaminophosphine, and mixtures thereof.

Preferred catalysts include the sulfonic acids, Lewis acids, methanesulfonic acid, AMBERYLST® 15, acidic versions of DOWEX®, DOWEX® AMBERYLST® 15 and methanesulfonic acid, being the most preferred.

Mixtures of catalysts are also within the scope of the present invention.

The catalysts are preferably employed at amounts of about 0.1 mol % to about 50.0 mol %, more preferably from about 0.1 mol % to about 25.0 mol %, even more preferably from about 0.1 mol % to about 20.0 mol %, even more preferably still from about 0.1 mol % to about 10.0 mol %, even more preferably still from about 0.2 mol % to about 10.0 mol %. Other suitable catalysts can be found in U.S. Pat. No. 4,272,394, and in PCT publications, WO 94/22800, WO 93/04153, WO96/00253 and WO 98/17379 all of which are incorporated herein by reference.

In one embodiment of this aspect of the present invention the reaction is conducted in the presence of a suitable solvent, or mixtures of solvents, such as, benzene, toluene, hexane, dichloromethane, tetrahydrofuran, dioxane, diethylether, methyl tert-butylether, or the like. Lastly, the reaction is preferably conducted at temperatures ranging from about −20° C. to about 300° C., and more preferably from about −10° C. to about 250° C.

In another embodiment of this aspect of the present invention the step of reacting alcohol with alkoxylated alcohol is conducted in the absence of a solvent.

Further disclosure on suitable solvents and catalysts can be found in "Advanced Organic Chemistry", by Jerry March, 4$^{th}$ ed., Wiley-Interscience Publisher, 1992, the relevant portions of which are incorporated herein by reference.

A representative synthetic route of this aspect of the invention is demonstrated via the following diagram.

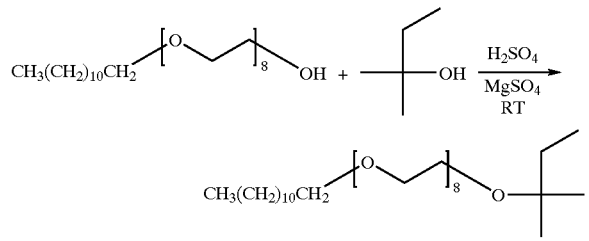

In one aspect of the present invention the surfactants of the present invention may be prepared by reacting an alpha olefin with an alkoxylated alcohol of the formula RO(R$^1$O)$_x$H wherein R, R$^1$, and x, are as defined above to form the ether-capped poly(oxyalkylated) alcohol of the formula:

RO(R$^1$O)$_x$R$^2$

In this aspect of the present invention the alpha olefin is selected such that upon addition to the alkoxylated alcohol of the formula RO(R$^1$O)$_x$OH, it is becomes R$^2$. Another way of saying this is that R$^2$ is a radical derived from an alpha olefin, or alpha olefin equivalent heterocycles. Examples of suitable alpha olefin equivalent heterocycles include, but not limited to, 3,4-dihydro-2H-pyran, 3,4-dihydro-2H-furan, 2-pyrroline, 3,4-dihydro-2H-thiophene. Examples of other suitable alpha olefins would include 1-pentene, 1-hexene, 3,3-dimethyl-1-pentene. For example, suitable alpha olefins would include, but not limited to:

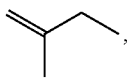

which would produce R$^2$ of the formula

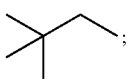

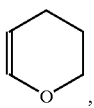

which would produce R$^2$ of the formula

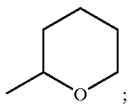

In one embodiment of this aspect of the present invention the step of reacting the alpha olefin with the alkoxylated alcohol is conducted in the presence of a catalyst. Suitable catalysts include Lewis acids; acids and their salts, both organic and inorganic; pyridinium salts; polymers; clays, such as, Spanish sepiolite clay, GIRDLER K-10; aluminosilicates or zeolites, such as HZS-360 zeolite, H-Y zeolite; activated carbon, such as sulfonated charcoal; transition metal complexes, such as, molybedenyl(VI) acetylacetone; transition metal salts, such as lanthum trichloride, ceric ammonium nitrate; 2,3-dichloro-5,6,dicyano-p-benzoquinone; bis(trimethysilyl)sulfate, and mixtures thereof.

Suitable Lewis acids include, but are not limited to, TiCl$_4$, Ti(OPr)$_4$, ZnCl$_2$, SnCl$_2$, AlCl$_3$, platinum dichloride, copper (II) chloride, phosphorous pentachloride, phosphorous trichloride, cobalt(II) chloride, zinc oxide, iron(II) chloride and BF$_3$.OEt$_2$.

Suitable inorganic acids and their salts include, mineral acids, such as, phosphoric acid, sulfuric acid, hydrochloric acid, phosphorous oxychloride, aluminium phosphate and ammonium chloride. Furthermore, the mineral acids or their salts can optionally be adsorbed on to a substrate, such as, silica gel, or alumina. For example sulfuric acid adsorbed on silica gel, or alumina impregnated with zinc chloride.

Suitable organic acids and their salts include: carboxylic acids, such as, acetic acid, oxalic acid, glycolic acid, citric acid, tartaric acid, glycolic acid, maleic acid and oxydisuccinic acid; halogenated carboxylic acids, such as, trifluoroacetic acid, heptaflurobutyric acid, dichloroacetic acid, and trichloroacetic acid; and sulfonic and sulfinic acids and their salts such as, p-toluenesulfonic acid, p-toluenesulfinic acid, methanesulfonic acid, 4-bromobenzenesulfonic acid, naphthalenesulfonic acid, (±)-10-camphorsulfonic and isomers, and alkylbenzenesulfonic acid, xylenesulfonic acid and cumenesulfonic acid.

Suitable pyridinium salts, include, but are not limited to, pyridinium p-toluenesulfonate (PPTS), pyridinium p-toluenesulfinate, pyridinium hydrochloride, pyridinium hydrobromide, pyridinium hydrogen bisulfate, pyridinium hydrogen sulfate and mixtures thereof.

Suitable transition metal, include, but are not limited to, molybedenyl(VI) acetylacetone; transition metal salts, such as lanthum trichloride, ceric ammonium nitrate; 2,3-dichloro-5,6,dicyano-p-benzoquinone, mercury(II) acetate, mercury(II)trifluroacetate, copper(II) acetylacetonate and teteracarbonylbis(cyclopentadienyl)diiron.

Suitable polymers, include, but are not limited to, polymeric ion exchange resins, or polyvinyl pyridines. Suitable polymeric ion exchange resins include those of the Amberylst series, such as AMBERYLST® 15, available from Rohm & Haas, the DOWEX® series, such as, DOWEX 50X8-50 available from Dow; REILLEX 424, available from Reilly Industries; the Amberlite series, such as AMBERLITE IRA-400, or AMBERLITE IR-118, available from Rohm & Haas; available from United Catalyst; the ENVIROCAT series, such as ENVIROCAT EPZG, available from Contract Chemicals; and combinations thereof. Suitable polyvinyl pyridines can be unsubstituted or substituted, such as substituted on the vinyl group and/or on the pyridine ring. Examples of suitable polyvinyl pyridines include, but are not limited to, poly(4-vinylpyridine trifluoromethanesulfonate), poly(2-vinylpyridine trifluoromethanesulfonate), poly(4-vinylpyridine p-toluenesulfonate), poly(2-vinylpyridine p-toluenesulfonate), poly(4-vinylpyridine chloride), poly(2-vinylpyridine chloride), poly(4-vinylpyridine bromide), poly(2-vinylpyridine bromide), and mixtures thereof. These polymeric catalysts have the additional advantage of being easy to separate from the surfactant produced.

Other suitable catalysts include, bis(trimethysilyl)sulfate, iodotrimethylsilane, allytrimethyl silane, hexamethyldisilane, iodine, bromine, iron(II) sulfate, triphenylphosphine, aluminium sulfate, alkylether sulfuric acids, alkyl sulfuric acids, lithium perchlorate, lithium teterafluoroborate, acetyltriphenylphosphonium bromide, zirconium hydroxide, potassium cyanide, and platinum oxide.

Preferred catalysts include the sulfonic acids, Lewis acids, polyvinyl pyridines, methanesulfonic acid, AMBERYLST® 15, acidic versions of DOWEX® and pyridinium p-toluenesulfonate (PPTS) with polyvinyl pyridines, pyridinium p-toluenesulfonate (PPTS), DOWEX® AMBERYLST® 15 and methanesulfonic acid, being the most preferred.

Mixtures of catalysts are also within the scope of the present invention. Similarly, the uses of supported, such as in a column for a continuous reaction, and unsupported catalysts are also within the scope of the present invention.

In another embodiment of this aspect of the present invention the catalyst can be of the zeolitic type. These type of catalysts can control the resulting product distribution in such a way that ether formation occurs mainly in the 2-position. This can be true regardless of the olefin type i.e. internal or alpha. Catalyst of this type are typically represented by the acidic zeolites which have the ability to rapidly isomerize olefin positions and exhibit shape selectivity due to their restricted pore size. Examples of these suitable catalysts include, but are not limited to, acidic zeolites such as H-ferrierite, acidic Mordenites, offretite, H-ZSM-12, acidic beta zeolites. HF treated forms of zeolites such as the above examples are also suitable. Examples of commercially available mordenite catalysts include Zeocat™ FM-8/25H, available from UOP.

The catalysts are preferably employed at amounts of about 0.1 mol % to about 50.0 mol %, more preferably from about 0.1 mol % to about 25.0 mol %, even more preferably from about 0.1 mol % to about 20.0 mol %, even more preferably still from about 0.1 mol % to about 10.0 mol %, even more preferably still from about 0.2 mol % to about 10.0 mol %. Other suitable catalysts can be found in U.S. Pat. No. 4,272,394, and in PCT publications, WO 94/22800, WO 93/04153, WO96/00253 and WO 98/17379 all of which are incorporated herein by reference.

In another embodiment of this aspect of the present invention the step of reacting the alpha olefin with an alkoxylated alcohol is conducted in the absence of a catalyst.

In one embodiment of this aspect of the present invention the reaction is conducted in the presence of a suitable solvent, or mixtures of solvents, such as benzene, toluene, dichloromethane, tetrahydrofuran, dioxane, diethylether, methyl tert-butylether, or the like. Lastly, the reaction is preferably conducted at temperatures ranging from about −20° C. to about 300° C., and more preferably from about −10° C. to about 250° C.

In another embodiment of this aspect of the present invention the step of reacting the alpha olefin with an alkoxylated alcohol is conducted in the absence of a solvent.

Further disclosure on suitable solvents and catalysts can be found in "Advanced Organic Chemistry", by Jerry March, 4$^{th}$ ed., Wiley-Interscience, 1992, "Comprehensive Organic Transformations" by Richard C. Larock, VCH Publishers, 1989, and "Protective Groups in Organic Synthesis" 3$^{RD}$ ed. by Theodora W. Greene and Peter G. M. Wuts, Wiley-Interscience, 1999 the relevant portions of which are incorporated herein by reference.

One representative synthetic route of this aspect of the invention is demonstrated via the following diagram.

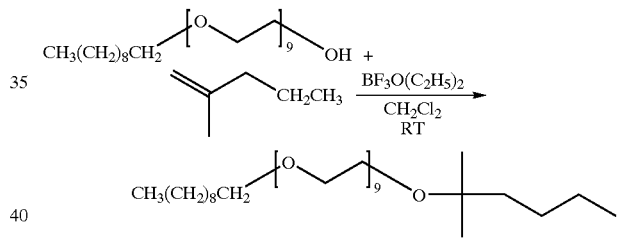

Another representative synthetic route of this aspect of the invention is demonstrated via the following diagram.

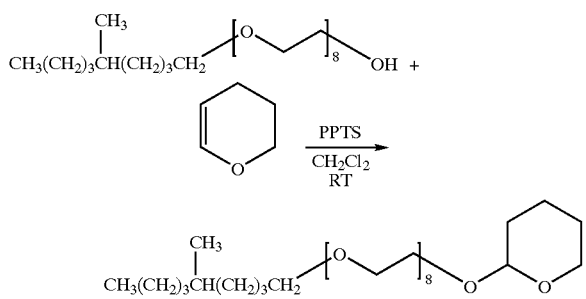

The ether-capped poly(oxyalkylated) alcohol surfactant product is then collect by means common in the art such as extraction. If desired, the surfactant may be further treated by stripping, distillation or various other means before use. The surfactants made by the process disclosed herein may contain related impurities which will not adversely affect performance.

Cleaning Adjunct Materials and Methods

In general, cleaning adjunct is any material required to transform a composition containing only the minimum essential ingredients into a composition useful for cleaning purposes, such as fabric cleaning, tableware cleaning, hard surface cleaning, or personal cleansing (such as a body wash or a shampoo). In preferred embodiments, cleaning adjuncts are easily recognizable to those of skill in the art as being absolutely characteristic of cleaning products, especially of cleaning products intended for direct use by a consumer in a domestic environment.

The precise nature of these additional components, and levels of incorporation thereof, will depend on the physical form of the composition and the nature of the cleaning operation for which it is to be used.

Preferably, the adjunct ingredients if used with bleach should have good stability therewith. Certain preferred detergent compositions herein should be boron-free and/or phosphate-free as required by legislation. Levels of adjuncts are from about 0.00001% to about 99.9%, by weight of the compositions. Use levels of the overall compositions can vary widely depending on the intended application, ranging for example from a few ppm in solution to so-called "direct application" of the neat cleaning composition to the surface to be cleaned.

Common adjuncts include builders, co-surfactants, enzymes, polymers, bleaches, bleach activators, catalytic materials and the like excluding any materials already defined hereinabove as part of the essential component of the inventive compositions. Other adjuncts herein can include diverse active ingredients or specialized materials, for example, dispersant polymers (e.g., from BASF Corp. or Rohm & Haas), color speckles, silvercare, anti-tarnish and/or anti-corrosion agents, dyes, fillers, germicides, bactericides, alkalinity sources, hydrotropes, anti-oxidants, enzyme stabilizing agents, suds boosters, buffers, anti-fungal agents, mildew control agents, insect repellents, anti-corrosive aids, chelants suds suppressors thickeners, abrasives, pro-perfumes, perfumes, solubilizing agents, carriers, processing aids, pigments, and, for liquid formulations, solvents, as described in detail hereinafter.

Co-surfactants

The surfactant system of the compositions according to the present invention may further comprise additional surfactants, herein also referred to as co-surfactants, preferably selected from: anionic surfactants, preferably selected from the group of alkyl alkoxylated sulfates, alkyl sulfates, alkyl disulfates, and/or linear alkyl benzenesulfonate surfactants; cationic surfactants, preferably selected from quaternary ammonium surfactants; nonionic surfactants, preferably alkyl ethoxylates, alkyl polyglucosides, polyhydroxy fatty acid amides, and/or amine or amine oxide surfactants; amphoteric surfactants, preferably selected from betaines and/or polycarboxylates (for example polyglycinates); and zwiterionic surfactants.

A wide range of these co-surfactants can be used in the cleaning compositions of the present invention. A typical listing of anionic, nonionic, ampholytic and zwitterionic classes, and species of these co-surfactants, is given in U.S. Pat. No. 3,664,961 issued to Norris on May 23, 1972. Amphoteric surfactants are also described in detail in "Amphoteric Surfacants, Second Edition", E. G. Lomax, Editor (published 1996, by Marcel Dekker, Inc.). Suitable surfactants can be found in WO 97/39087, WO 97/39088, WO 97/39091, WO 98/23712, WO 97/38972, WO 97/39-89, WO 97/39090, WO 99/19434, WO 99/18929, WO 99/18928, WO 99/19448, WO 99/19449, WO 99/05243, WO 99/05242, WO 99/05244, WO 99/05082, WO 99/05084, WO 99/05241, WO 99/07656, WO 00/23549, and WO 00/23548, all of which are incorporated in by reference.

The compositions of the present invention preferably comprise from about 0.01% to about 55%, more preferably from about 0.1% to about 45%, more preferably from about 0.25% to about 30%, more preferably from about. 0.5% to about 20%, by weight of co-surfactants. Selected co-surfactants are further identified as follows.

(1) Anionic Co-surfactants

Nonlimiting examples of anionic co-surfactants useful herein, typically at levels from about 0.1% to about 50%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^- M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alpha-sulfonated fatty acid esters, the $C_{10}$–$C_{18}$ sulfated alkyl polyglycosides, the $C_{10}$–$C_{18}$ alkyl alkoxy sulfates ("$AE_xS$"; especially EO 1-7 ethoxy sulfates), and $C_{10}$–$C_{18}$ alkyl alkoxy carboxylates (especially the EO 1-5 ethoxycarboxylates). The $C_{12}$–$C_{18}$ betaines and sulfobetaines ("sultaines"), $C_{10}$–$C_{18}$ amine oxides, and the like, can also be included in the overall compositions. $C_{10}$–$C_{20}$ conventional soaps may also be used. If high sudsing is desired, the branched-chain $C_{10}$–$C_{16}$ soaps may be used. Other conventional useful anionic co-surfactants are listed in standard texts.

Other suitable anionic surfactants that can be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

Another type of useful surfactants are the so-called dianionics. These are surfactants which have at least two anionic groups present on the surfactant molecule. Some suitable dianionic surfactants are further described in WO 98/00498, WO 98/00503, U.S. Pat. No. 5,958,858, WO 98/05742, and WO 98/05749, the disclosures of which are incorporated herein by reference.

Additionally and preferably, the surfactant may be a branched alkyl sulfate, branched alkyl alkoxylate, or branched alkyl alkoxylate sulfate. These surfactants are further described in WO 99/19434, WO 99/18929, WO 99/18928, WO 99/19448, and WO 99/19449. Other suitable mid-chain branched Surfacants can be found in WO 97/39087, WO 97/39088, WO 97/39091, WO 98/23712, WO 97/38972, WO 97/39-89, and WO 97/39090. Mixtures of these branched surfactants with conventional linear surfactants are also suitable for use in the present compositions.

Additionally, the surfactant may be a modified alkylbenzene sulfonate surfactants, or MLAS. Suitable MLAS surfactants can be found in WO 99/05243, WO 99/05242, WO 99/05244, WO 99/05082, WO 99/05084, WO 99/05241, WO 99/07656, WO 00/23549, and WO 00/23548.

The anionic surfactants useful in the LDL of the present invention are preferably selected from the group consisting of, linear alkylbenzene sulfonate, alpha olefin sulfonate, paraffin sulfonates, alkyl ester sulfonates, alkyl sulfates, alkyl alkoxy sulfate, alkyl sulfonates, alkyl alkoxy carboxylate, alkyl alkoxylated sulfates, sarcosinates, taurinates, and mixtures thereof. An effective amount, typically from about 0.5% to about 90%, preferably about 5% to about 50%, more preferably from about 10 to about 30%, by weight of anionic detersive surfactant can be used in the LDL compositions of the present invention.

When included therein, the laundry detergent compositions of the present invention typically comprise from about 0.1% to about 50%, preferably from about 1% to about 40% by weight of an anionic surfactant.

(2) Nonionic Co-surfactants

Nonlimiting examples of nonionic co-surfactants useful herein typically at levels from about 0.1% to about 50%, by weight include the alkoxylated alcohols (AE's) and alkyl phenols, polyhydroxy fatty acid amides (PFAA's), alkyl polyglycosides (APG's), $C_{10}$–$C_{18}$ glycerol ethers, and the like.

Examples of commercially available nonionic surfactants of this type include: Tergitol™ 15-S-9 (the condensation product of $C_{11}$–$C_{15}$ linear alcohol with 9 moles ethylene oxide) and Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide). Neodol™ 23-3 (the condensation product of $C_{12}$–$C_{13}$ linear alcohol with 3 moles of ethylene oxide), Neodol™ 45-7 (the condensation product of $C_{14}$–$C_{15}$ linear alcohol with 7 moles of ethylene oxide) and Neodol™ 45-5 (the condensation product of $C_{14}$–$C_{15}$ linear alcohol with 5 moles of ethylene oxide) marketed by Shell Chemical Company; Kyro™ EOB (the condensation product of $C_{13}$–$C_{15}$ alcohol with 9 moles ethylene oxide), marketed by The Procter & Gamble Company; and Genapol LA O3O or O5O (the condensation product of $C_{12}$–$C_{14}$ alcohol with 3 or 5 moles of ethylene oxide) marketed by Hoechst. The preferred range of HLB in these AE nonionic surfactants is from 8–17 and most preferred from 8–14. Condensates with polyoxypropylene oxide and butylene oxides may also be used.

Another class of preferred nonionic co-surfactants for use herein are the polyhydroxy fatty acid amide surfactants of the formula.

wherein $R^1$ is H, or $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Typical examples include the $C_{12}$–$C_{18}$ and $C_{12}$–$C_{14}$ N-methylglucamides. See U.S. Pat. Nos. 5,194,639 and 5,298,636. N-alkoxy polyhydroxy fatty acid amides can also be used; see U.S. Pat. No. 5,489,393.

Also useful as a nonionic co-surfactant in the present invention are the alkylpolysaccharides such as those disclosed in U.S. Pat. No. 4,565,647, Llenado, issued Jan. 21, 1986.

Preferred alkylpolyglycosides have the formula

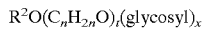

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position. Compounds of this type and their use in detergent are disclosed in EP-B 0 070 077, 0 075 996 and 0 094 118.

Polyethylene, polypropylene, and polybutylene oxide condensates of alkyl phenols are also suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X45, X-114, X-100 and X-102, all marketed by the Rohm & Haas Company. These surfactants are commonly referred to as alkylphenol alkoxylates (e.g., alkyl phenol ethoxylates).

The condensation products of ethylene oxide with a hydrophobic base formed by the condensation of propylene oxide with propylene glycol are also suitable for use as the additional nonionic surfactant in the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

When the composition is an automatic dishwashing composition (ADW), it preferably contains a nonionic co-surfactants. In general, bleach-stable nonionic co-surfactants are preferred These nonionic co-surfactants when present, are included at levels of from about 0.1% to about 15% of the composition. The nonionic co-surfactant may be a low cloud point nonionic co-surfactant, a high cloud point nonionic co-surfactant or mixtures thereof. One preferred ADW composition of the present invention, includes a low cloud point nonionic co-surfactant, and/or a high cloud point nonionic co-surfactant in addition to the surfactant of the present invention. Nonionic surfactants generally are well known, being described in more detail in Kirk Othmer's Encyclopedia of Chemical Technology, 3rd Ed., Vol. 22, pp. 360–379, "Surfactants and Detersive Systems", incorporated by reference herein.

"Cloud point", as used herein, is a well known property of nonionic surfactants which is the result of the surfactant becoming less soluble with increasing temperature, the temperature at which the appearance of a second phase is observable is referred to as the "cloud point" (See Kirk Othmer, pp. 360–362, hereinbefore).

As used herein, a "low cloud point" nonionic co-surfactant is defined as a nonionic surfactant system ingredient having a cloud point of less than 30° C., preferably less than about 20° C., and most preferably less than about 10° C. Typical low cloud point nonionic co-surfactants include nonionic alkoxylated surfactants, especially ethoxylates derived from primary alcohol, and polyoxypropylene/polyoxyethylene/polyoxypropylene (PO/EO/PO) reverse block polymers. Also, such low cloud point nonionic co-surfactants include, for example, ethoxylated-propoxylated alcohol (e.g., Olin Corporation's Poly-Tergent® SLF18) and epoxy-capped poly(oxyalkylated) alcohols (e.g., Olin Corporation's Poly-Tergent® SLF18B series of nonionics, as described, for example, in WO 94/22800, published Oct. 13, 1994 by Olin Corporation).

Nonionic co-surfactants can optionally contain propylene oxide in an amount up to about 15% by weight. Other preferred nonionic co-surfactants can be prepared by the processes described in U.S. Pat. No. 4,223,163, issued Sep. 16, 1980, Builloty, incorporated herein by reference.

Low cloud point nonionic co-surfactants additionally comprise a polyoxyethylene, polyoxypropylene block polymeric compound. Block polyoxyethylene-polyoxypropylene polymeric compounds include those based on ethylene glycol, propylene glycol, glycerol, trimethylolpropane and ethylenediamine as initiator reactive hydrogen compound. Certain of the block polymer surfactant compounds designated PLURONIC®, REVERSED PLURONIC®, and TETRONIC® by the BASF-Wyandotte Corp., Wyandotte, Michigan, are suitable in ADD compositions of the invention. Preferred examples include REVERSED PLURONIC® 25R2 and TETRONIC® 702, Such co-surfactants are typically useful herein as low cloud point nonionic surfactants.

As used herein, a "high cloud point" nonionic co-surfactant is defined as a nonionic surfactant system ingredient having a cloud point of greater than 40° C., preferably greater than about 50° C., and more preferably greater than about 60° C. Preferably the nonionic co-surfactant system comprises an ethoxylated surfactant derived from the reaction of a monohydroxy alcohol or alkylphenol containing from about 8 to about 20 carbon atoms, with from about 6 to about 15 moles of ethylene oxide per mole of alcohol or alkyl phenol on an average basis. Such high cloud point nonionic co-surfactants include, for example, Tergitol 15S9 (supplied by Union Carbide), Rhodasurf TMD 8.5 (supplied by Rhone Poulenc), and Neodol 91-8 (supplied by Shell).

It is also preferred for purposes of the present invention that the high cloud point nonionic co-surfactant further have a hydrophile-lipophile balance ("HLB"; see Kirk Othmer hereinbefore) value within the range of from about 9 to about 15, preferably 11 to 15. Such materials include, for example, Tergitol. 15S9 (supplied by Union Carbide), Rhodasurf TMD 8.5 (supplied by Rhone Poulenc), and Neodol 91-8 (supplied by Shell).

Another preferred high cloud point nonionic co-surfactant is derived from a straight or preferably branched chain or secondary fatty alcohol containing from about 6 to about 20 carbon atoms ($C_6$–$C_{20}$ alcohol), including secondary alcohols and branched chain primary alcohols. Preferably, high cloud point nonionic co-surfactants are branched or secondary alcohol ethoxylates, more preferably mixed C9/11 or C11/15 branched alcohol ethoxylates, condensed with an average of from about 6 to about 15 moles, preferably from about 6 to about 12 moles, and most preferably from about 6 to about 9 moles of ethylene oxide per mole of alcohol. Preferably the ethoxylated nonionic co-surfactant so derived has a narrow ethoxylate distribution relative to the average.

When the optional co-surfactants are a mixture of low cloud point nonionics and high cloud point nonionics it is preferred that the mixture is combined in a weight ratio preferably within the range of from about 10:1 to about 1:10.

Also preferred nonionics are amine oxide surfactants. The compositions of the present invention may comprise amine oxide in accordance with the general formula I:

$$R^1(EO)_x(PO)_y(BO)_zN(O)(CH_2R')_2 \cdot qH_2O \qquad (I).$$

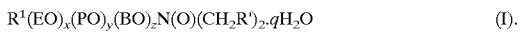

In general, it can be seen that the structure (I) provides one long-chain moiety $R^1(EO)_x(PO)_y(BO)_z$ and two short chain moieties, $CH_2R'$. R' is preferably selected from hydrogen, methyl and —$CH_2OH$. In general $R^1$ is a primary or branched hydrocarbyl moiety which can be saturated or unsaturated, preferably, $R^1$ is a primary alkyl moiety. When x+y+z=0, $R^1$ is a hydrocarbyl moiety having chainlength of from about 8 to about 18. When x+y+z is different from 0, $R^1$ may be somewhat longer, having a chainlength in the range $C_{12}$–$C_{24}$. The general formula also encompasses amine oxides wherein x+y+z =0, $R_1$=$C_8$–$C_{18}$, R'=H and q=0–2, preferably 2. These amine oxides are illustrated by $C_{12-14}$ alkyldimethyl amine oxide, tetradecyldimethyl amine oxide, hexadecyl dimethylamine oxide, octadecylamine oxide and their hydrates, especially the dihydrates as disclosed in U.S. Pat. Nos. 5,075,501 and 5,071,594, incorporated herein by reference.

The invention also encompasses amine oxides wherein x+y+z is different from zero, specifically x+y+z is from about 1 to about 10, $R^1$ is a primary alkyl group containing 8 to about 24 carbons, preferably from about 12 to about 16 carbon atoms; in these embodiments y+z is preferably 0 and x is preferably from about 1 to about 6, more preferably from about 2 to about 4; EO represents ethyleneoxy; PO represents propyleneoxy; and BO represents butyleneoxy. Such amine oxides can be prepared by conventional synthetic methods, e.g., by the reaction of alkylethoxysulfates with dimethylamine followed by oxidation of the ethoxylated amine with hydrogen peroxide.

Highly preferred amine oxides herein are solutions at ambient temperature. Amine oxides suitable for use herein are made commercially by a number of suppliers, including Akzo Chemie, Ethyl Corp., and Procter & Gamble. See McCutcheon's compilation and Kirk-Othmer review article for alternate amine oxide manufacturers.

Whereas in certain of the preferred embodiments R' is H, there is some latitude with respect to having R' slightly larger than H. Specifically, the invention further encompasses embodiments wherein R' is $CH_2OH$, such as hexadecylbis(2-hydroxyethyl)amine oxide, tallowbis(2-hydroxyethyl)amine oxide, stearylbis(2-hydroxyethyl) amine oxide and oleylbis(2-hydroxyethyl)amine oxide, dodecyldimethylamine oxide dihydrate.

In another embodiment of this aspect of the present invention the compositions may contain amine oxides with linear or branched alkyl chain lengths of 10–22 with 14–18 more preferred. In another embodiment of this aspect of the present invention the amine oxides may be branched amine oxides with an of average carbon count 16/17, for example the branched alkyl chain could be isostearyl.

(3) Cationic Co-surfactants

Nonlimiting examples of cationic co-surfactants useful herein typically at levels from about 0.1% to about 50%, by weight include the choline ester-type quats and alkoxylated quaternary ammonium (AQA) surfactant compounds, and the like. Most preferred for aqueous liquid compositions herein are soluble cationic co-surfactants which do not readily hydrolyze in the product.

Cationic co-surfactants useful as a component of the surfactant system is a cationic choline ester-type quat surfactant which are preferably water dispersible compounds having surfactant properties and comprise at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529.

Cationic ester surfactants include those having the formula:

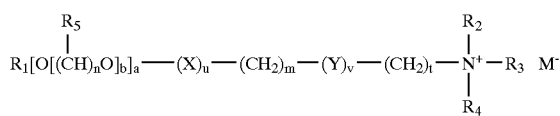

wherein $R_1$ is a $C_5$–$C_{31}$ linear or branched alkyl, alkenyl or alkaryl chain or $M^-.N^+(R_6R_7R_8)(CH_2)_s$; X and Y, independently, are selected from the group consisting of COO, OCO, O, CO, OCOO, CONH, NHCO, OCONH and NHCOO wherein at least one of X or Y is a COO, OCO, OCOO, OCONH or NHCOO group; $R_2$, $R_3$, $R^4$, $R_6$, $R_7$ and $R_8$ are independently selected from the group consisting of alkyl, alkenyl, hydroxyalkyl, hydroxyalkenyl and alkaryl groups having from 1 to 4 carbon atoms; and $R_5$ is independently H or a $C_1$–$C_3$ alkyl group; wherein the values of m, n, s and t independently lie in the range of from 0 to 8, the value of b lies in the range from 0 to 20, and the values of a, u and v independently are either 0 or 1 with the proviso that at least one of u or v must be 1; and wherein M is a counter anion.

Preferably $R_2$, $R_3$ and $R_4$ are independently selected from $CH_3$ and —$CH_2CH_2OH$.

Preferably M is selected from the group consisting of halide, methyl sulfate, sulfate, and nitrate, more preferably methyl sulfate, chloride, bromide or iodide.

Preferred water dispersible cationic ester surfactants are the choline esters having the formula:

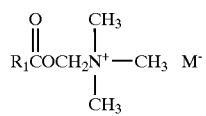

wherein $R^1$ is a $C_{11}$–$C_{19}$ linear or branched alkyl chain.

Particularly preferred choline esters of this type include the stearoyl choline ester quaternary methylammonium halides ($R^1$=$C_{17}$ alkyl), palmitoyl choline ester quaternary methylammonium halides ($R^1$=$C_{15}$ alkyl), myristoyl choline ester quaternary methylammonium halides ($R^1$=$C_{11}$ alkyl), cocoyl choline ester quaternary methylammonium halides ($R^1$=$C_{11}$–$C_{13}$ alkyl), tallowyl choline ester quaternary methylammonium halides ($R^1$=$C_{15}$–$C_{17}$ alkyl), and any mixtures thereof.

The particularly preferred choline esters, given above, may be prepared by the direct esterification of a fatty acid of the desired chain length with dimethylaminoethanol, in the presence of an acid catalyst. The reaction product is then quaternized with a methyl halide, preferably in the presence of a solvent such as ethanol, propylene glycol or preferably a fatty alcohol ethoxylate such as $C_{10}$–$C_{18}$ fatty alcohol ethoxylate having a degree of ethoxylation of from 3 to 50 ethoxy groups per mole forming the desired cationic material. They may also be prepared by the direct esterification of a long chain fatty acid of the desired chain length together with 2-haloethanol, in the presence of an acid catalyst material. The reaction product is then quaternized with trimethylamine, forming the desired cationic material.

In a preferred aspect these cationic ester surfactant are hydrolysable under the conditions of a laundry wash method.

Cationic co-surfactants useful herein also include alkoxylated quaternary ammonium (AQA) surfactant compounds (referred to hereinafter as "AQA compounds") having the formula:

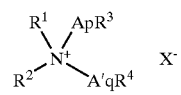

I wherein $R^1$ is an alkyl or alkenyl moiety containing from about 8 to about 18 carbon atoms, preferably 10 to about 16 carbon atoms, most preferably from about 10 to about 14 carbon atoms; $R^2$ is an alkyl group containing from one to three carbon atoms, preferably methyl; $R^3$ and $R^4$ can vary independently and are selected from hydrogen (preferred), methyl and ethyl; $X^-$ is an anion such as chloride, bromide, methylsulfate, sulfate, or the like, sufficient to provide electrical neutrality. A and A' can vary independently and are each selected from $C_1$–$C_4$ alkoxy, especially ethoxy (i.e., —$CH_2CH_2O$—), propoxy, butoxy and mixed ethoxy/propoxy; p is from 0 to about 30, preferably 1 to about 4 and q is from 0 to about 30, preferably 1 to about 4, and most preferably to about 4; preferably both p and q are 1. See also: EP 2,084, published May 30, 1979, by The Procter & Gamble Company, which describes cationic co-surfactants of this type which are also useful herein.

The levels of the AQA surfactants used to prepare finished laundry detergent compositions typically range from about 0.1% to about 5%, preferably from about 0.45% to about 2.5%, by weight.

Polymeric Suds Stabilizer

The compositions of the present invention may optionally contain a polymeric suds stabilizer. These polymeric suds stabilizers provide extended suds volume and suds duration without sacrificing the grease cutting ability of the liquid detergent compositions. These polymeric suds stabilizers are selected from:

i) homopolymers of (N,N-dialkylamino)alkyl acrylate esters having the formula:

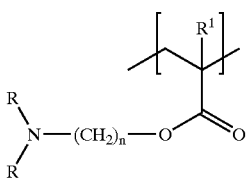

wherein each R is independently hydrogen, $C_1$–$C_8$ alkyl, and mixtures thereof, $R^1$ is hydrogen, $C_1$–$C_6$ alkyl, and mixtures thereof, n is from 2 to about 6; and ii) copolymers of (i) and

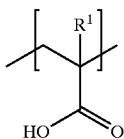

wherein $R^1$ is hydrogen, $C_1$–$C_6$ alkyl, and mixtures thereof, provided that the ratio of (ii) to (i) is from about 2 to 1 to about 1 to 2; The molecular weight of the polymeric suds boosters, determined via conventional gel permeation chromatography, is from about 1,000 to about 2,000,000, preferably from about 5,000 to about 1,000,000, more preferably from about 10,000 to about 750,000, more preferably from about 20,000 to about 500,000, even more preferably from about 35,000 to about 200,000. The polymeric suds stabilizer can optionally be present in the form of a salt, either an inorganic or organic salt, for example the citrate, sulfate, or nitrate salt of (N,N-dimethylamino)alkyl acrylate ester.

One preferred polymeric suds stabilizer is (N,N-dimethylamino)alkyl acrylate esters, namely

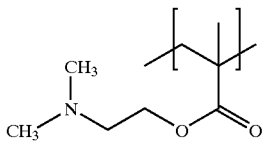

When present in the compositions, the polymeric suds booster may be present in the composition from about 0.01% to about 15%, preferably from about 0.05% to about 10%, more preferably from about 0.1 % to about 5%, by weight.

Other suitable polymeric suds stabilizers, including protenacious suds stabilizers and zwitterionic suds stabilizers, can be found in WO 99/27058, WO 99/27054, WO 99/27053, WO 99/27057. Also suitable are the cationic copolymer stabilizers, which can be found in U.S. Pat. No. 4,454,060.

Enzymes

Detergent compositions of the present invention may further comprise one or more enzymes which provide cleaning performance benefits. Said enzymes include enzymes selected from cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, β-glucanases, arabinosidases or mixtures thereof. A preferred combination is a detergent composition having a cocktail of conventional applicable enzymes like protease, amylase, lipase, cutinase and/or cellulase. Enzymes when present in the compositions, at from about 0.0001% to about 5% of active enzyme by weight of the detergent composition.

Proteolytic Enzyme

The proteolytic enzyme can be of animal, vegetable or microorganism (preferred) origin. The proteases for use in the detergent compositions herein include (but are not limited to) trypsin, subtilisin, chymotrypsin and elastase-type proteases. Preferred for use herein are subtilisin-type proteolytic enzymes. Particularly preferred is bacterial serine proteolytic enzyme obtained from *Bacillus subtilis* and/or *Bacillus licheniformis*.

Suitable proteolytic enzymes include Novo Industri A/S Alcalase® (preferred), Esperase®, Savinase® (Copenhagen, Denmark), Gist-brocades' Maxatase®, Maxacal® and Maxapem 15® (protein engineered Maxacal®) (Delft, Netherlands), and subtilisin BPN and BPN' (preferred), which are commercially available. Preferred proteolytic enzymes are also modified bacterial serine proteases, such as those made by Genencor International, Inc. (San Francisco, Calif.) which are described in European Patent 251,446B, granted Dec. 28, 1994 (particularly pages 17, 24 and 98) and which are also called herein "Protease B". U.S. Pat. No. 5,030,378, Venegas, issued Jul. 9, 1991, refers to a modified bacterial serine proteolytic enzyme (Genencor International) which is called "Protease A" herein (same as BPN'). In particular see columns 2 and 3 of U.S. Pat. No. 5,030,378 for a complete description, including amino sequence, of Protease A and its variants. Other proteases are sold under the tradenames: Primase, Durazym, Opticlean and Optimase. Preferred proteolytic enzymes, then, are selected from the group consisting of Alcalase® (Novo Industri A/S), BPN', Protease A and Protease B (Genencor), and mixtures thereof. Protease B is most preferred.

Of particular interest for use herein are the proteases described in U.S. Pat. No. 5,470,733.

Also proteases described in WO 95/10591 can be included in the detergent composition of the invention.

Another preferred protease, referred .a) as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +127, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in WO 95/10615 published Apr. 20, 1995 by Genencor International (A. Baeck et al. entitled "Protease-Containing Cleaning Compositions" having U.S. Ser. No. 08/322,676, filed Oct. 13, 1994).

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Protease enzyme may be incorporated into the compositions in accordance with the invention at a level of from 0.0001% to 2% active enzyme by weight of the composition.

Amylase

Amylases (α and/or β) can be included for removal of carbohydrate-based stains. Suitable amylases are Termamyl® (Novo Nordisk), Fungamyl® and BAN® (Novo Nordisk). The enzymes may be of any suitable origin, such as vegetable, animal, bacterial, fungal and yeast origin. Amylase enzymes are normally incorporated in the detergent composition at levels from 0.0001% to 2%, preferably from about 0.0001% to about 0.5%, more preferably from about 0.0005% to about 0.1%, even more preferably from about 0.001% to about 0.05% of active enzyme by weight of the detergent composition.

Amylase enzymes also include those described in WO95/26397 and in WO 96/23873.

One suitable amylase enzyme is NATALASE® available from Novo Nordisk.

Other amylases suitable herein include, for example, α-amylases described in GB 1,296,839 to Novo; RAPIDASE®, International Bio-Synthetics, Inc. and TERMAMYL®, Novo. FUNGAMYL® from Novo is especially useful.

Particularly preferred amylases herein include amylase variants having additional modification in the immediate parent as described in WO 95/0603 A and are available from the assignee, Novo, as DURAMYL®. Other particularly preferred oxidative stability enhanced amylase include those described in WO 94/8314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Various carbohydrase enzymes which impart antimicrobial activity may also be included in the present invention. Such enzymes include endoglycosidase, Type II endoglycosidase and glucosidase as disclosed in U.S. Pat. Nos. 5,041,236, 5,395,541, 5,238,843 and 5,356,803 the disclosures of which are herein incorporated by reference. Of course, other enzymes having antimicrobial activity may be employed as well including peroxidases, oxidases and various other enzymes.

It is also possible to include an enzyme stabilization system into the compositions of the present invention when any enzyme is present in the composition.

Various carbohydrase enzymes which impart antimicrobial activity may also be included in the present invention. Such enzymes include endoglycosidase, Type II endoglycosidase and glucosidase as disclosed in U.S. Pat. Nos. 5,041,236, 5,395,541, 5,238,843 and 5,356,803 the disclosures of which are herein incorporated by reference. Of course, other enzymes having antimicrobial activity may be employed as well including peroxidases, oxidases and various other enzymes.

It is also possible to include an enzyme stabilization system into the compositions of the present invention when any enzyme is present in the composition.

Peroxidase enzymes can be used in combination with oxygen sources, e.g., percarbonate, perborate, persulfate, hydrogen peroxide, etc. They are typically used for "solution bleaching," i.e. to prevent transfer of dyes or pigments removed from substrates during wash operations to other substrates in the wash solution. Peroxidase enzyme are known in the art, and include, for example, horseradish peroxidase, ligninase, and haloperoxidase such as chloro- and bromo-peroxidase. Peroxidase-containing detergent compostions are disclosed, for example, in PCT International Application WO 89/09813, published Oct. 19, 1989, by O. Kirk, assigned to Novo Industries A/S. The present invention encompasses peroxidase-free automatic dishwashing composition embodiments.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

The enzymes may be incorporated into detergent compositions herein in the form of suspensions, "marumes" or "prills". Another suitable type of enzyme comprises those in the form of slurries of enzymes in nonionic surfactants, e.g., the enzymes marketed by Novo Nordisk under the tradename "SL" or the microencapsulated enzymes marketed by Novo Nordisk under the tradename "LDP."

Enzymes added to the compositions herein in the form of conventional enzyme prills are especially preferred for use herein. Such prills will generally range in size from about 100 to 1,000 microns, more preferably from about 200 to 800 microns and will be suspended throughout the non-aqueous liquid phase of the composition. Prills in the compositions of the present invention have been found, in comparison with other enzyme forms, to exhibit especially desirable enzyme stability in terms of retention of enzymatic activity over time. Thus, compositions which utilize enzyme prills need not contain conventional enzyme stabilizing such as must frequently be used when enzymes are incorporated into aqueous liquid detergents.

If employed, enzymes will normally be incorporated into the non-aqueous liquid compositions herein at levels sufficient to provide up to about 10 mg by weight, more typically from about 0.01 mg to about 5 mg, of active enzyme per gram of the composition. Stated otherwise, the non-aqueous liquid detergent compositions herein will typically comprise from about 0.001% to 5%, preferably from about 0.01% to 1% by weight, of a commercial enzyme preparation. Protease enzymes, for example, are usually present in such commercial preparations at levels sufficient to provide from 0.005 to 0.1 Anson units (AU) of activity per gram of composition.

Enzyme Stabilizing System

The enzyme-containing compositions herein may optionally also comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

Perfumes

Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual perfumery ingredients can comprise from about 0.0001% to about 90% of a finished perfume composition.

Dispersant Polymer

The compositions of the present invention may additionally contain a dispersant polymer. When present, a dispersant polymer in the instant compositions is typically at levels in the range from 0 to about 25%, preferably from about 0.5% to about 20%, more preferably from about 1% to about 8% by weight of the composition. Dispersant polymers are useful for improved filming performance of the present compositions, especially in higher pH embodiments, such as those in which wash pH exceeds about 9.5. Particularly preferred are polymers which inhibit the deposition of calcium carbonate or magnesium silicate on dishware.

Dispersant polymers suitable for use herein are further illustrated by the film-forming polymers described in U.S. Pat. No. 4,379,080 (Murphy), issued Apr. 5, 1983.

Suitable polymers are preferably at least partially neutralized or alkali metal, ammonium or substituted ammonium (e.g., mono-, di- or triethanolammonium) salts of polycarboxylic acids. The alkali metal, especially sodium salts are most preferred. While the molecular weight of the polymer can vary over a wide range, it preferably is from about 1,000 to about 500,000, more preferably is from about 1,000 to about 250,000, and most preferably, especially if the composition is for use in North American automatic dishwashing appliances, is from about 1,000 to about 5,000.

Other suitable dispersant polymers include those disclosed in U.S. Pat. Nos. 3,308,067, 4,530,766, 3,723,322, 3,929,107, 3,803,285. 3,629,121, 4,141,841, and 5,084,535.

Copolymers of acrylamide and acrylate having a molecular weight of from about 3,000 to about 100,000, preferably from about 4,000 to about 20,000, and an acrylamide content of less than about 50%, preferably less than about 20%, by weight of the dispersant polymer can also be used.

Particularly preferred dispersant polymers are low molecular weight modified polyacrylate copolymers.

Suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and is the fully neutralized form of the polymer comprising about 70% by weight acrylic acid and about 30% by weight methacrylic acid.

Other dispersant polymers useful herein include the polyethylene glycols and polypropylene glycols having a molecular weight of from about 950 to about 30,000 which can be obtained from the Dow Chemical Company of Midland, Mich.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Yet another group of acceptable dispersants are the organic dispersant polymers, such as polyaspartate.

Material Care Agents

When the compositions of the present invention are automatic dishwashing compositions they may contain one or more material care agents which are effective as corrosion inhibitors and/or anti-tarnish aids. Such materials are preferred components of machine dishwashing compositions especially in certain European countries where the use of electroplated nickel silver and sterling silver is still comparatively common in domestic flatware, or when aluminium protection is a concern and the composition is low in silicate. Generally, such material care agents include metasilicate, silicate, bismuth salts, manganese salts, paraffin, triazoles, pyrazoles, thiols, mercaptans, aluminium fatty acid salts, and mixtures thereof.

When present, such protecting materials are preferably incorporated at low levels, e.g., from about 0.01% to about 5% of the composition. Suitable corrosion inhibitors include paraffin oil, typically a predominantly branched aliphatic hydrocarbon having a number of carbon atoms in the range of from about 20 to about 50; preferred paraffin oil is selected from predominantly branched $C_{25-45}$ species with a ratio of cyclic to noncyclic hydrocarbons of about 32:68. A paraffin oil meeting those characteristics is sold by Wintershall, Salzbergen, Germany, under the trade name WINOG 70. Additionally, the addition of low levels of bismuth nitrate (i.e., $Bi(NO_3)_3$) is also preferred.

Other corrosion inhibitor compounds include benzotriazole and comparable compounds; mercaptans or thiols including thionaphtol and thioanthranol; and finely divided Aluminium fatty acid salts, such as aluminium tristearate. The formulator will recognize that such materials will generally be used judiciously and in limited quantities so as to avoid any tendency to produce spots or films on glassware or to compromise the bleaching action of the compositions. For this reason, mercaptan anti-tarnishes which are quite strongly bleach-reactive and common fatty carboxylic acids which precipitate with calcium in particular are preferably avoided.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetrace-tates, N-hydroxyethylethylenediaminetriacetates, nitrilotriacetates, ethylenediamine tetrapro-prionates, triethylenetetraaminehexacetates, diethylenetriaminepentaacetates, and ethanoldi-glycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder. Similarly, the so called "weak" builders such as citrate can also be used as chelating agents.

If utilized, these chelating agents will generally comprise from about 0.1% to about 15% by weight of the detergent compositions herein. More preferably, if utilized, the chelating agents will comprise from about 0.1% to about 3.0% by weight of such compositions.

Composition pH

The surfactants of the present invention may be used in compositions which cover a wide range, from acidic to basic and all shades in-between. The compositions of the present invention can have a pH from 2 to 12. If a composition with a pH greater than 7 is to be more effective, it preferably should contain a buffering agent capable of providing a generally more alkaline pH in the composition and in dilute solutions, i.e., about 0.1% to 0.4% by weight aqueous solution, of the composition. The pKa value of this buffering agent should be about 0.5 to 1.0 pH units below the desired pH value of the composition (determined as described above). Preferably, the pKa of the buffering agent should be from about 7 to about 10. Under these conditions the buffering agent most effectively controls the pH while using the least amount thereof. Similarly, an acidic buffering system can be employed to maintain the compositions pH.

The buffering agent may be an active detergent in its own right, or it may be a low molecular weight, organic or inorganic material that is used in this composition solely for maintaining an alkaline pH. One type of preferred buffering agents for compositions of this invention are nitrogen-containing materials. Some examples are amino acids such as lysine or lower alcohol amines like mono-, di-, and tri-ethanolamine. Other preferred nitrogen-containing buffering agents are Tri(hydroxymethyl)amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Mixtures of any of the above are also acceptable. Useful inorganic buffers/alkalinity sources include the alkali metal carbonates and alkali metal phosphates, e.g., sodium carbonate, sodium polyphosphate. Also suitable are organic acids like citric acid, acetic acid and the like. For additional buffers see McCutcheon's EMULSIFIERS AND DETERGENTS, North American Edition, 1997, McCutcheon Division, MC Publishing Company Kirk and WO 95/07971 both of which are incorporated herein by reference.

One highly preferred group of buffers, especially in LDL compositions, are diamines. Preferred organic diamines are those in which pK1 and pK2 are in the range of about 8.0 to about 11.5, preferably in the range of about 8.4 to about 11, even more preferably from about 8.6 to about 10.75. Preferred materials for performance and supply considerations are 1,3-bis(methylamine)-cyclohexane, 1,3 propane diamine (pK1=10.5; pK2=8.8), 1,6 hexane diamine (pK1=11; pK2=10), 1,3 pentane diamine (Dytek EP) (pK1=10.5; pK2=8.9), 2-methyl 1,5 pentane diamine (Dytek A) (pK1=11.2; pK2=10.0). Other preferred materials are the primary/primary diamines with alkylene spacers ranging from C4 to C8. In general, it is believed that primary diamines are preferred over secondary and tertiary diamines.

Definition of pK1 and pK2

As used herein, "pKa1" and "pKa2" are quantities of a type collectively known to those skilled in the art as "pKa"

pKa is used herein in the same manner as is commonly known to people skilled in the art of chemistry. Values referenced herein can be obtained from literature, such as from "Critical Stability Constants: Volume 2, Amines" by Smith and Martel, Plenum Pregs, NY and London, 1975. Additional information on pKa's can be obtained from relevant company literature, such as information supplied by Dupont, a supplier of diamines. More detailed information of pKa's can be found in U.S. Pat. No. 5,990,065.

Examples of preferred diamines include the following: dimethyl aminopropyl amine, 1,6-hexane diamine, 1,3 propane diamine, 2-methyl 1,5 pentane diamine, 1,3-Pentanediamine, 1,3-diaminobutane, 1,2-bis(2-aminoethoxy)ethane, Isophorone diamine, 1,3-bis (methylamine)-cyclohexane and mixtures thereof.

The buffer can be complemented (i.e. for improved sequestration in hard water) by other optional detergency builder salts selected from nonphosphate detergency builders known in the art, which include the various water-soluble, alkali metal, ammonium or substituted ammonium borates, hydroxysulfonates, polyacetates, and polycarboxylates. Preferred are the alkali metal, especially sodium, salts of such materials. Alternate water-soluble, non-phosphorus organic builders can be used for their sequestering properties. Examples of polyacetate and polycarboxylate builders are the sodium, potassium, lithium, ammonium and substituted ammonium salts of ethylenediamine tetraacetic acid; nitrilotriacetic acid, tartrate monosuccinic acid, tartrate disuccinic acid, oxydisuccinic acid, carboxymethoxysuccinic acid, mellitic acid, and sodium benzene polycarboxylate salts.

The buffering agent, if used, is present in the compositions of the invention herein at a level of from about 0.1% to 15%, preferably from about 1% to 10%, most preferably from about 2% to 8%, by weight of the composition. If the optional buffer used is a diamine, the composition will preferably contain at least about 0.1%, more preferably at least about 0.2%, even more preferably, at least about 0.25%, even more preferably still, at least about 0.5% by weight of said composition of diamine. The composition will also preferably contain no more than about 15%, more preferably no more than about 10%, even more preferably, no more than about 6%, even more preferably, no more than about 5%, even more preferably still, no more than about 1.5% by weight of said composition of diamine.

Water-Soluble Silicates

The present compositions may further comprise water-soluble silicates. Water-soluble silicates herein are any silicates which are soluble to the extent that they do not adversely affect spotting/filming characteristics of the composition.

Examples of silicates are sodium metasilicate and, more generally, the alkali metal silicates, particularly those having a $SiO_2:Na_2O$ ratio in the range 1.6:1 to 3.2:1; and layered silicates, such as the layered sodium silicates described in U.S. Pat. No. 4,664,839, issued May 12, 1987 to H. P. Rieck. NaSKS-6™ is a crystalline layered silicate marketed by Hoechst (commonly abbreviated herein as "SKS-6"). Unlike zeolite builders, Na SKS-6 and other water-soluble silicates usefule herein do not contain aluminum. NaSKS6 is the $\delta-Na_2SiO_5$ form of layered silicate and can be prepared by methods such as those described in German DE-A-3,417,649 and DE-A-3,742,043. SKS-6 is a preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used. Various other layered silicates from Hoechst include NaSKS-5, NaSKS-7 and NaSKS-11, as the α-, β-and γ-forms. Other silicates may also be useful, such as for example magnesium silicate, which can serve as a crispening agent in granular formulations, as a stabilizing agent for oxygen bleaches, and as a component of suds control systems.

Silicates particularly useful in automatic dishwashing (ADD) applications include granular hydrous 2-ratio silicates such as BRITESIL® H20 from PQ Corp., and the commonly sourced BRITESIL® H24 though liquid grades of various silicates can be used when the ADD composition has liquid form. Within safe limits, sodium metasilicate or sodium hydroxide alone or in combination with other silicates may be used in an ADD context to boost wash pH to a desired level.

Bleaching Compounds

Bleaching Agents and Bleach Activators

The compositions herein preferably further contain a bleach and/or a bleach activators. Bleaches agents will typically, when present, be at levels of from about 1% to about 30%, more typically from about 5% to about 20%, of the detergent composition, especially for fabric laundering. If present, the amount of bleach activators will typically be from about 0.1% to about 60%, more typically from about 0.5% to about 40% of the composition comprising the bleaching agent-plus-bleach activator.

The bleaches used herein can be any of the bleaches useful for detergent compositions in textile cleaning, hard surface cleaning, or other cleaning purposes that are now known or become known. These include oxygen bleaches as well as other bleaching agents. Perborate bleaches, e.g., sodium perborate (e.g., mono- or tetra-hydrate) can be used herein. Also suitable are organic or inorganic peracids. Suitable organic or inorganic peracids for use herein include: percarboxylic acids and salts; percarbonic acids and salts; perimidic acids and salts; peroxymonosulfuric acids and salts; persulphates such as monopersulfate; peroxyacids such as diperoxydodecandioic acid (DPDA): magnesium perphthalic acid; perlauric acid; phthaloyl amidoperoxy caproic acid (PAP); perbenzoic and alkylperbenzoic acids; and mixtures thereof.

One class of suitable organic peroxycarboxylic acids have the general formula:

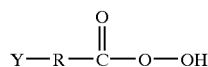

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted acid has the general formula:

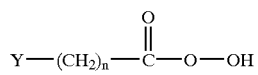

where Y can be, for example, H, $CH_3$, $CH_2Cl$, C(O)OH, or C(O)OOH; and n is an integer from 1 to 20. When the organic peroxycarboxylic acid is aromatic, the unsubstituted acid has the general formula:

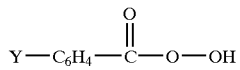

wherein Y can be, for example, hydrogen, alkyl, alkylhalogen, halogen, C(O)OH or C(O)OOH.

Typical monoperoxy acids useful herein include alkyl and aryl peroxyacids such as:
(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);
(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);
(iii) amidoperoxyacids, e.g. mononoylamide of either peroxysuccinic acid (NAPSA) or of peroxyadipic acid (NAPAA).

Typical diperoxyacids useful herein include alkyl diperoxyacids and aryldiperoxyacids, such as:
(iv) 1,12-diperoxydodecanedioic acid;
(v) 1,9-diperoxyazelaic acid;
(vi) diperoxybrassylic acid; diperoxysebacic acid and diperoxyisophthalic acid;
(vii) 2-decyidiperoxybutane-1,4-dioic acid;
(viii) 4,4'-sulfonylbisperoxybenzoic acid.

Such bleaching agents are disclosed in U.S. Pat. No. 4,483,781, Hartman, issued Nov. 20, 1984, U.S. Pat. No. 4,634,551 to Burns et al., European Patent Application 0,133,354, Banks et al. published Feb. 20, 1985, and U.S. Pat. No. 4,412,934, Chung et al. issued Nov. 1, 1983. Sources also include 6-nonylamino-6-oxoperoxycaproic acid as described in U.S. Pat. No. 4,634,551, issued Jan. 6, 1987 to Burns et al. Persulfate compounds such as for example OXONE, manufactured commercially by E.I. DuPont de Nemours of Wilmington, Del. can also be employed as a suitable source of peroxymonosulfuric acid.

Particularly preferred peracid compounds are those having the formula:

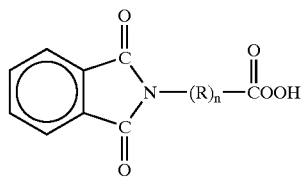

wherein R is $C_{1-4}$ alkyl and n is an integer of from 1 to 5. A particularly preferred peracid has the formula where R is $CH_2$ and n is 5 i.e.; phthaloylamino peroxy caproic acid (PAP) as described in U.S. Pat. Nos. 5,487,818, 5,310,934, 5,246,620, 5,279,757 and 5,132,431. PAP is available from Ausimont SpA under the tradename Euroco.

The peracids used herein preferably have a solubility in aqueous liquid compositions measured at 20° C. of from about 10 ppm to about 1500 ppm, more preferably from about 50 ppm to about 1000 ppm, most preferably from about 50 ppm to about 800 ppm solubility is measured at 20° C.

In a particularly preferred embodiment of the present invention the peracid has mean average particle size of less than 100 microns, more preferably less than 80 microns, even more preferably less than 60 microns. Most preferably, when the peracid is PAP, it has a mean average particle size of between about 20 and about 50 microns.

Alternatively, although not preferred, the bleach can be a chlorine bleach. Chlorine bleaches can be any convenient conventional chlorine bleach. Such compounds are often divided in to two categories namely, inorganic chlorine bleaches and organic chlorine bleaches. Examples of the former are hypochlorites, such as sodium hypochlorite, calcium hypochlorite, potassium hypochlorite, magnesium hypochlorite. Another example of an inorganic chlorine bleach usable in the present invention is chlorinated trisodium phosphate dodecahydrate. Examples of the latter are isocyanurates, such as potassium dichloroisocyanurate, sodium dichloroisocyanurate. Examples of other organic chlorine bleaches usable in the present invention are 1,3-dichloro-5,5-dimethlhydantoin, N-chlorosulfamide, chloramine T, Dichloramine T, chloramine B, Dichloramine T, N,N'-dichlorobenzoylene urea, paratoluene sulfondichoroamide, trichloromethylamine, N-chloroammeline, N-chlorosuccinimide, N,N'-dichloroazodicarbonamide, N-chloroacetyl urea, N,N'-dichlorobiuret and chlorinated dicyandamide. Preferably the chlorine bleach is an inorganic chlorine bleach, more preferably it is sodium hypochlorite.

Another category of bleaches that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxydodecanedioic acid. Such bleaches are disclosed in U.S. Pat. No. 4,483,781, Hartman, issued Nov. 20, 1984, U.S. patent application Ser. No. 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaches also include 6-nonylamino-6-oxoperoxycaproic acid as described in U.S. Pat. No. 4,634,551, issued Jan. 6, 1987 to Burns et al.

Peroxygen bleaches can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Mixtures of bleaches can also be used.

Peroxygen bleaches, the perborates, the percarbonates, etc., are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Bleach Activators

Bleach activators useful herein include amides, imides, esters and anhydrides. Commonly at least one substituted or unsubstituted acyl moiety is present, covalently connected to a leaving group as in the structure R—C(O)—L. In one preferred mode of use, bleach activators are combined with a source of hydrogen peroxide, such as the perborates or percarbonates, in a single product. Conveniently, the single product leads to in situ production in aqueous solution (i.e., during the washing process) of the percarboxylic acid corresponding to the bleach activator. The product itself can be hydrous, for example a powder, provided that water is controlled in amount and mobility such that storage stability is acceptable. Alternately, the product can be an anhydrous solid or liquid. In another mode, the bleach activator or oxygen bleach is incorporated in a pretreatment product, such as a stain stick; soiled, pretreated substrates can then be exposed to further treatments, for example of a hydrogen peroxide source. With respect to the above bleach activator structure RC(O)L, the atom in the leaving group connecting to the peracid-forming acyl moiety R(C)O— is most typically O or N. Bleach activators can have non-charged, positively or negatively charged peracid-forming moieties and/or noncharged, positively or negatively charged leaving groups. One or more peracid-forming moieties or leaving-groups can be present. See, for example, U.S. Pat. Nos. 5,595,967, 5,561,235, 5,560,862 or the bis-(peroxycarbonic) system of U.S. Pat. No. 5,534,179. Mixtures of suitable bleach activators can also be used. Bleach activators can be substituted with electron-donating or electron-releasing moieties either in the leaving-group or in the peracid-forming moiety or moieties, changing their reactivity and making them more or less suited to particular pH or wash conditions. For example, electron-withdrawing groups such as $NO_2$ improve the efficacy of bleach activators intended for use in mild-pH (e.g., from about 7.5- to about 9.5) wash conditions.

An extensive and exhaustive disclosure of suitable bleach activators and suitable leaving groups, as well as how to determine suitable activators, can be found in U.S. Pat. Nos. 5,686,014 and 5,622,646.

Cationic bleach activators include quaternary carbamate-, quaternary carbonate-, quaternary ester- and quaternary amide-types, delivering a range of cationic peroxyimidic, peroxycarbonic or peroxycarboxylic acids to the wash. An analogous but non-cationic palette of bleach activators is available when quaternary derivatives are not desired. In more detail, cationic activators include quaternary ammonium-substituted activators of WO 96-06915, U.S. Pat. No. 4,751,015 and 4,397,757, EP-A-284292, EP-A-331, 229 and EP-A-03520. Also useful are cationic nitriles as disclosed in EP-A-303,520 and in European Patent Specification 458,396 and 464,880. Other nitrile types have electron-withdrawing substituents as described in U.S. Pat. No. 5,591,378.

Other bleach activator disclosures include GB 836,988; 864,798; 907,356; 1,003,310 and 1,519,351; German Patent 3,337,921; EP-A-0185522; EP-A-0174132; EP-A-0120591; U.S. Pat. Nos. 1,246,339; 3,332,882; 4,128,494; 4,412,934 and 4,675,393, and the phenol sulfonate ester of alkanoyl aminoacids disclosed in U.S. Pat. No. 5,523,434. Suitable bleach activators include any acetylated diamine types, whether hydrophilic or hydrophobic in character.

Of the above classes of bleach precursors, preferred classes include the esters, including acyl phenol sulfonates, acyl alkyl phenol sulfonates or acyl oxybenzenesulfonates (OBS leaving-group); the acyl-amides; and the quaternary ammonium substituted peroxyacid precursors including the cationic nitriles.

Preferred bleach activators include N,N,N'N'-tetraacetyl ethylene diamine (TAED) or any of its close relatives including the triacetyl or other unsymmetrical derivatives. TAED and the acetylated carbohydrates such as glucose pentaacetate and tetraacetyl xylose are preferred hydrophilic bleach activators. Depending on the application, acetyl triethyl citrate, a liquid, also has some utility, as does phenyl benzoate.

Preferred hydrophobic bleach activators include sodium nonanoyloxybenzene sulfonate (NOBS or SNOBS), N-(alkanoyl)aminoalkanoyloxy benzene sulfonates, such as 4-[N-(nonanoyl)aminohexanoyloxy]-benzene sulfonate or (NACA-OBS) as described in U.S. Pat. No. 5,534,642 and in EPA 0 355 384 A1, substituted amide types described in detail hereinafter, such as activators related to NAPAA, and activators related to certain imidoperacid bleaches, for example as described in U.S. Pat. No. 5,061,807, issued Oct. 29, 1991 and assigned to Hoechst Aktiengesellschaft of Frankfurt, Germany and Japanese Laid-Open Patent Application (Kokai) No. 4-28799.

Another group of peracids and bleach activators herein are those derivable from acyclic imidoperoxycarboxylic acids and salts thereof, See U.S. Pat. No. 5,415,796, and cyclic imidoperoxycarboxylic acids and salts thereof, see U.S. Pat. Nos. 5,061,807, 5,132,431, 5,654,269, 5,246,620, 5,419,864 and 5,438,147.

Other suitable bleach activators include sodium-4-benzoyloxy benzene sulfonate (SBOBS); sodium-1-methyl-2-benzoyloxy benzene-4-sulphonate; sodium-4-methyl-3-benzoyloxy benzoate (SPCC); trimethyl ammonium toluyloxy-benzene sulfonate; or sodium 3,5,5-trimethyl hexanoyloxybenzene sulfonate (STHOBS).

Bleach activators may be used in an amount of up to 20%, preferably from 0.1–10% by weight, of the composition, though higher levels, 40% or more, are acceptable, for example in highly concentrated bleach additive product forms or forms intended for appliance automated dosing.

Highly preferred bleach activators useful herein are amide-substituted and an extensive and exhaustive disclosure of these activators can be found in U.S. Pat. Nos. 5,686,014 and 5,622,646.

Other useful activators, disclosed in U.S. Pat. No. 4,966,723, are benzoxazin-type, such as a $C_6H_4$ ring to which is fused in the 1,2-positions a moiety —C(O)OC($R^1$)=N—. A highly preferred activator of the benzoxazin-type is:

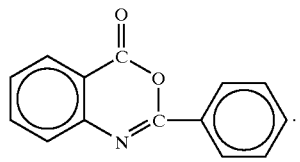

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators are very useful herein, especially the acyl caprolactams (see for example WO 94-28102 A) and acyl valerolactams (see U.S. Pat. No. 5,503,639). See also U.S. Pat. No. 4,545,784 which discloses acyl caprolactams, including benzoyl caprolactam adsorbed into sodium perborate. In certain preferred embodiments of the invention, NOBS, lactam activators, imide activators or amide-functional activators, especially the more hydrophobic derivatives, are desirably combined with hydrophilic activators such as TAED, typically at weight ratios of hydrophobic activator: TAED in the range of 1:5 to 5:1, preferably about 1:1. Other suitable lactam activators are alpha-modified, see WO 96-22350 A1, Jul. 25, 1996. Lactam activators, especially the more hydrophobic types, are desirably used in combination with TAED, typically at weight ratios of amido-derived or caprolactam activators:TAED in the range of 1:5 to 5:1, preferably about 1:1. See also the bleach activators having cyclic amidine leaving-group disclosed in U.S. Pat. No. 5,552,556.

Nonlimiting examples of additional activators useful herein are to be found in U.S. Pat. Nos. 4,915,854, 4,412,934 and 4,634,551. The hydrophobic activator nonanoyloxybenzene sulfonate (NOBS) and the hydrophilic tetraacetyl ethylene diamine (TAED) activator are typical, and mixtures thereof can also be used.

Additional activators useful herein include those of U.S. Pat. No. 5,545,349, which is also incorporated herein by reference.

Bleaches other than oxygen bleaching agents are also known in the art and can be utilized herein. One type of non-oxygen bleaching agent of particular interest includes photoactivated bleaches such as the sulfonated zinc and/or aluminum phthalocyanines. See U.S. Pat. No. 4,033,718, issued Jul. 5, 1977 to Holcombe et al. If used, detergent compositions will typically contain from about 0.025% to about 1.25%, by weight, of such bleaches, especially sulfonate zinc phthalocyanine.

Bleach Catalysts

The present invention compositions and methods may optionally utilize metal-containing bleach catalysts that are effective for use in ADD, laundry or bleaching compositions. Preferred are manganese and cobalt-containing bleach catalysts.

For examples of suitable bleach catalysts see U.S. Pat. Nos. 4,246,612, 5,804542, 5,798,326, 5,246,621, 4,430,243, 5,244,594, 5,597,936, 5,705,464, 4,810,410, 4,601,845, 5,194,416, 5,703,030, 4,728,455, 4,711,748, 4,626,373, 4,119,557, 5,114,606, 5,599,781, 5,703,034, 5,114,611, 4,430,243, 4,728,455, and 5,227,084; EP Pat. Nos. 408,131, 549,271, 384,503, 549,272, 224,952, and 306,089; DE Pat. No. 2,054,019; CA Pat No. 866,191.

Preferred are cobalt (III) catalysts having the formula:

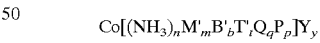

wherein cobalt is in the +3 oxidation state; n is an integer from 0 to 5 (preferably 4 or 5; most preferably 5); M' represents a monodentate ligand; m is an integer from 0 to 5 (preferably 1 or 2; most preferably 1); B' represents a bidentate ligand; b is an integer from 0 to 2; T' represents a tridentate ligand; t is 0 or 1; Q is a tetradentate ligand; q is 0 or 1; P is a pentadentate ligand; p is 0 or 1; and n+m+2b+3t+4q+5p=6; Y is more appropriately selected counteranions present in a number y, where y is an integer from 1 to 3 (preferably 2 to 3; most preferably 2 when Y is a −1 charged anion), to obtain a charge-balanced salt, preferred Y are selected from the group consisting of chloride, iodide, $I_3^-$, formate, nitrate, nitrite, sulfate, sulfite, citrate, acetate, malonate, succinate, adipate, maleate, carbonate, bromide, $PF_6^-$, $BF_4^-$, $B(Ph)_4^-$, phosphate, phosphite, silicate, tosylate, methanesulfonate, and the like and combinations thereof [optionally, Y can be protonated if more than one anionic group exists in Y, e.g., $HPO_4^{2-}$, $HCO_3^-$, $H_2PO_4^-$, etc., and further, Y may be selected from the group consisting of non-traditional inorganic anions such as anionic surfactants, e.g., linear alkylbenzene sulfonates (LAS), alkyl sulfates (AS), alkylethoxysulfonates (AES), etc., and/or anionic polymers, e.g., polyacrylates, polymethacrylates, etc.]; and wherein further at least one of the coordination sites attached to the cobalt is labile under automatic dishwashing use conditions and the remaining coordination sites stabilize the cobalt under automatic dishwashing conditions such that the reduction potential for cobalt (III) to cobalt (II) under alkaline conditions is less than about 0.4 volts (preferably less than about 0.2 volts) versus a normal hydrogen electrode.

Preferred cobalt catalysts of this type have the formula:

$$[CO(NH_3)_n(M')_m]Y_y$$

wherein n is an integer from 3 to 5 (preferably 4 or 5; most preferably 5); M' is a labile coordinating moiety, preferably selected from the group consisting of chlorine, bromine, hydroxide, water, and (when m is greater than 1) combinations thereof; m is an integer from 1 to 3 (preferably 1 or 2; most preferably 1); m+n=6; and Y is an appropriately selected counteranion present in a number y, which is an integer from 1 to 3 (preferably 2 to 3; most preferably 2 when Y is a −1 charged anion), to obtain a charge-balanced salt.

The preferred cobalt catalyst of this type useful herein are cobalt pentaamine chloride salts having the formula [Co(NH$_3$)$_5$Cl]Y$_y$, and especially [Co(NH$_3$)$_5$Cl]Cl$_2$.

More preferred are the present invention compositions which utilize cobalt (III) bleach catalysts having the formula:

$$[Co(NH_3)_n(M)_m(B)_b]T_y$$

wherein cobalt is in the +3 oxidation state; n is 4 or 5 (preferably 5); M is one or more ligands coordinated to the cobalt by one site; m is 0, 1 or 2 (preferably 1); B is a ligand coordinated to the cobalt by two sites; b is 0 or 1 (preferably 0), and when b=0, then m+n=6, and when b=1, then m=0 and n=4; and T is one or more appropriately selected counteranions present in a number y, where y is an integer to obtain a charge-balanced salt (preferably y is 1 to 3; most preferably 2 when T is a −1 charged anion); and wherein further said catalyst has a base hydrolysis rate constant of less than 0.23 M$^{-1}$ s$^{-1}$ (25° C.).

The most preferred cobalt catalyst useful herein are cobalt pentaamine acetate salts having the formula [Co(NH$_3$)$_5$OAc]T$_y$, wherein OAc represents an acetate moiety, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc](SO$_4$); [Co(NH$_3$)$_5$OAc](BF$_4$)$_2$; and [Co(NH$_3$)$_5$OAc](NO$_3$)$_2$.

As a practical matter, and not by way of limitation, the cleaning compositions and cleaning processes herein can be adjusted to provide on the order of at least one part per hundred million of the active bleach catalyst species, when present, in the aqueous washing medium, and will more preferably provide from about 0.01 ppm to about 25 ppm, more preferably from about 0.05 ppm to about 10 ppm, and most preferably from about 0.1 ppm to about 5 ppm, of the bleach catalyst species in the wash liquor. In order to obtain such levels in the wash liquor of an automatic dishwashing process, typical automatic dishwashing compositions herein will comprise from about 0.0005% to about 0.2%, more preferably from about 0.004% to about 0.08%, of bleach catalyst by weight of the cleaning compositions.

Builders

Builders can operate via a variety of mechanisms including forming soluble or insoluble complexes with hardness ions, by ion exchange, and by offering a surface more favorable to the precipitation of hardness ions than are the surfaces of articles to be cleaned. Builder level can vary widely depending upon end use and physical form of the composition. For example, high-surfactant formulations can be unbuilt. The level of builder can vary widely depending upon the end use of the composition and its desired physical form. The compositions will comprise at least about 0.1%, preferably from about 1% to about 90%, more preferably from about 5% to about 80%, even more preferably from about 10% to about 40% by weight, of the detergent builder. Lower or higher levels of builder, however, are not excluded.

Suitable builders herein can be selected from the group consisting of phosphates and polyphosphates, especially the sodium salts; carbonates, bicarbonates, sesquicarbonates and carbonate minerals other than sodium carbonate or sesquicarbonate; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions.

Builder mixtures, sometimes termed "builder systems" can be used and typically comprise two or more conventional builders, optionally complemented by chelants, pH-buffers or fillers, though these latter materials are generally accounted for separately when describing quantities of materials herein. In terms of relative quantities of surfactant and builder in the present granular compositions, preferred builder systems are typically formulated at a weight ratio of surfactant to builder of from about 60:1 to about 1:80. Certain preferred granular detergents have said ratio in the range 0.90:1.0 to 4.0:1.0, more preferably from 0.95:1.0 to 3.0:1.0.

P-containing detergent builders often preferred where permitted by legislation include, but are not limited to, the alkali metal, ammonium and alkanolammonium salts of polyphosphates exemplified by the tripolyphosphates, pyrophosphates, glassy polymeric meta-phosphates; and phosphonates. Where phosphorus-based builders can be au used, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used though such materials are more commonly used in a low-level mode as chelants or stabilizers.

Phosphate detergent builders for use in granular compositions are well known. They include, but are not limited to, the alkali metal, ammonium and alkanolammonium salts of polyphosphates (exemplified by the tripolyphosphates, pyrophosphates, and glassy polymeric meta-phosphates). Phosphate builder sources are described in detail in Kirk Othmer, 3rd Edition, Vol. 17, pp. 426–472 and in "Advanced Inorganic Chemistry" by Cotton and Wilkinson, pp. 394–400 (John Wiley and Sons, Inc.; 1972).

Preferred levels of phosphate builders herein are from about 10% to about 75%, preferably from about 15% to about 50%, of phosphate builder.

Phosphate builders can optionally be included in the compositions herein to assist in controlling mineral hardness. Builders are typically used in automatic dishwashing to assist in the removal of particulate soils.

Suitable carbonate builders include alkaline earth and alkali metal carbonates as disclosed in German Patent Application No. 2,321,001 published on Nov. 15, 1973, although sodium bicarbonate, sodium carbonate, sodium sesquicarbonate, and other carbonate minerals such as trona or any convenient multiple salts of sodium carbonate and calcium carbonate such as those having the composition $2Na_2CO_3.CaCO_3$ when anhydrous, and even calcium carbonates including calcite, aragonite and vaterite, especially forms having high surface areas relative to compact calcite may be useful, for example as seeds. Various grades and types of sodium carbonate and sodium sesquicarbonate may be used, certain of which are particularly useful as carriers for other ingredients, especially detersive surfactants.

Suitable organic detergent builders include polycarboxylate compounds, including water-soluble nonsurfactant dicarboxylates and tricarboxylates. More typically builder polycarboxylates have a plurality of carboxylate groups, preferably at least 3 carboxylates. Carboxylate builders can be formulated in acid, partially neutral, neutral or overbased form. When in salt form, alkali metals, such as sodium, potassium, and lithium, or alkanolammonium salts are preferred. Polycarboxylate builders include the ether polycarboxylates, such as oxydisuccinate, see Berg, U.S. Pat. No. 3,128,287, Apr. 7, 1964, and Lamberti et al, U.S. Pat. No. 3,635,830, Jan. 18, 1972; "TMS/TDS" builders of U.S. Pat. No. 4,663,071, Bush et al, May 5, 1987; and other ether carboxylates including cyclic and alicyclic compounds, such as those described in U.S. Pat. Nos. 3,923,679; 3,835,163; 4,158,635; 4,120,874 and 4,102,903.

Other suitable builders are the ether hydroxypolycarboxylates, copolymers of maleic anhydride with ethylene or vinyl methyl ether; 1,3,5-trihydroxy benzene-2,4,6-trisulphonic acid; carboxymethyloxysuccinic acid; the various alkali metal, ammonium and substituted ammonium salts of polyacetic acids such as ethylenediamine tetraacetic acid and nitrilotriacetic acid; as well as mellitic acid, succinic acid, oxydisuccinic acid, polymaleic acid, benzene 1,3,5-tricarboxylic acid, carboxymethyloxysuccinic acid, and soluble salts thereof.

Citrates, e.g., citric acid and soluble salts thereof are important carboxylate builders due to availability from renewable resources and biodegradability. Citrates can also be used in the present granular compositions, especially in combination with zeolite and/or layered silicates. Citrates can also be used in combination with zeolite, the hereafter mentioned BRITESIL types, and/or layered silicate builders. Oxydisuccinates are also useful in such compositions and combinations. Oxydisuccinates are also especially useful in such compositions and combinations.

Where permitted alkali metal phosphates such as sodium tripolyphosphates, sodium pyrophosphate and sodium orthophosphate can be used. Phosphonate builders such as ethane-1-hydroxy-1,1-diphosphonate and other known phosphonates, e.g., those of U.S. Pat. Nos. 3,159,581; 3,213,030; 3,422,021; 3,400,148 and 3,422,137 can also be used and may have desirable antiscaling properties.

Certain detersive surfactants or their short-chain homologs also have a builder action. For unambiguous formula accounting purposes, when they have surfactant capability, these materials are summed up as detersive surfactants. Preferred types for builder functionality are illustrated by: 3,3-dicarboxy-4-oxa-1,6-hexanedioates and the related compounds disclosed in U.S. Pat. No. 4,566,984, Bush, Jan. 28, 1986. Succinic acid builders include the $C_5$–$C_{20}$ alkyl and alkenyl succinic acids and salts thereof. Succinate builders also include: laurylsuccinate, myristylsuccinate, palmitylsuccinate, 2-dodecenylsuccinate (preferred), 2-pentadecenylsuccinate, and the like. Laurylsuccinates are described in European Patent Application 86200690.5/0,200,263, published Nov. 5, 1986. Fatty acids, e.g., $C_{12}$–$C_{18}$ monocarboxylic acids, can also be incorporated into the compositions as surfactant/builder materials alone or in combination with the aforementioned builders, especially citrate and/or the succinate builders, to provide additional builder activity but are generally not desired. Such use of fatty acids will generally result in a diminution of sudsing in laundry compositions, which may need to be taken into account by the formulator. Fatty acids or their salts are undesirable in Automatic Dishwashing (ADD) embodiments in situations wherein soap scums can form and be deposited on dishware. Other suitable polycarboxylates are disclosed in U.S. Pat. No. 4,144,226, Crutchfield et al, Mar. 13, 1979 and in U.S. Pat. No. 3,308,067, Diehl, Mar. 7, 1967. See also Diehl, U.S. Pat. No. 3,723,322.

Other types of inorganic builder materials which can be used have the formula $(M_x)_i Ca_y (CO_3)_z$ wherein x and i are integers from 1 to 15, y is an integer from 1 to 10, z is an integer from 2 to 25, $M_i$ are cations, at least one of which is a water-soluble, and the equation $\Sigma_{i=1-15}(x_i$ multiplied by the valence of $M_i)+2y=2z$ is satisfied such that the formula has a neutral or "balanced" charge. These builders are referred to herein as "Mineral Builders". Waters of hydration or anions other than carbonate may be added provided that the overall charge is balanced or neutral. The charge or valence effects of such anions should be added to the right side of the above equation. Preferably, there is present a water-soluble cation selected from the group consisting of hydrogen, water-soluble metals, hydrogen, boron, ammonium, silicon, and mixtures thereof, more preferably, sodium, potassium, hydrogen, lithium, ammonium and mixtures thereof, sodium and potassium being highly preferred. Nonlimiting examples of noncarbonate anions include those selected from the group consisting of chloride, sulfate, fluoride, oxygen, hydroxide, silicon dioxide, chromate, nitrate, borate and mixtures thereof. Preferred builders of this type in their simplest forms are selected from the group consisting of $Na_2Ca(CO_3)_2$, $K_2Ca(CO_3)_2$, $Na_2Ca_2(CO_3)_3$, $NaKCa(CO_3)_2$, $NaKCa_2(CO_3)_3$, $K_2Ca_2(CO_3)_3$, and combinations thereof. An especially preferred material for the builder described herein is $Na_2Ca(CO_3)_2$ in any of its crystalline modifications. Suitable builders of the above-defined type are further illustrated by, and include, the natural or synthetic forms of any one or combinations of the following minerals: Afghanite, Andersonite, AsheroftineY, Bcyerite, Borcaite, Burbankite, Butschliite, Canctinite, Carbocernaite, Carletonite, Davyne, DonnayiteY, Fairchildite, Ferrisurite, Franzinite, Gaudefroyite, Gaylussite, Girvasite, Gregoryite, Jouravskite, KamphaugiteY, Kettnerite, Khanneshite, LepersonniteGd, Liottite, MckelveyiteY, Microsommite, Mroseite, Natrofairchildite, Nycrereite, RemonditeCe, Sacrofanite, Schrockingerite, Shortite, Surite, Tunisite, Tuscanite, Tyrolite, Vishnevite, and Zemkorite. Preferred mineral forms include Nyererite, Fairchildite and Shortite.

Detergent builders can also be selected from aluminosilicates and silicates, for example to assist in controlling mineral, especially Ca and/or Mg, hardness in wash water or to assist in the removal of particulate soils from surfaces.

Suitable silicate builders include water-soluble and hydrous solid types and including those having chain-, layer-, or three-dimensional-structure as well as amorphous-solid or non-structured-liquid types. Preferred are alkali metal silicates, particularly those liquids and solids having a $SiO_2:Na_2O$ ratio in the range 1.6:1 to 3.2:1, including, particularly for automatic dishwashing purposes, solid hydrous 2-ratio silicates marketed by PQ Corp. under the tradename BRITESIL®, e.g., BRITESIL H2O; and layered silicates, e.g., those described in U.S. Pat. No. 4,664,839, May 12, 1987, H. P. Rieck. NaSKS-6, sometimes abbreviated "SKS-6", is a crystalline layered aluminium-free $\delta$-$Na_2SiO_5$ morphology silicate marketed by Hoechst and is preferred especially in granular laundry compositions. See preparative methods in German DE-A-3,417,649 and DE-A-3,742,043. Other layered silicates, such as those having the general formula $NaMSi_xO_{2x+1}.yH_2O$ wherein M is sodium or hydrogen, x is a number from 1.9 to 4, preferably 2, and y is a number from 0 to 20, preferably 0, can also or alternately be used herein. Layered silicates from Hoechst also include NaSKS-5, NaSKS-7 and NaSKS-11, as the $\alpha$, $\beta$ and $\gamma$ layer-silicate forms. Other silicates may also be useful, such as magnesium silicate, which can serve as a crispening agent in granules, as a stabilising agent for bleaches, and as a component of suds control systems.

Also suitable for use herein are synthesized crystalline ion exchange materials or hydrates thereof having chain structure and a composition represented by the following general formula in an anhydride form: $xM_2O.ySiO_2.zM'O$ wherein M is Na and/or K, M' is Ca and/or Mg; y/x is 0.5 to 2.0 and z/x is 0.005 to 1.0 as taught in U.S. Pat. No. 5,427,711, Sakaguchi et al, Jun. 27, 1995.

Aluminosilicate builders are especially useful in granular compositions, but can also be incorporated in liquids, pastes or gels. Suitable for the present purposes are those having empirical formula: $[M_z(AlO_2)_z(SiO_2)_v].xH_2O$ wherein z and v are integers of at least 6, the molar ratio of z to v is in the range from 1.0 to 0.5, and x is an integer from 15 to 264. Aluminosilicates can be crystalline or amorphous, naturally-occurring or synthetically derived. An aluminosilicate production method is in U.S. Pat. No. 3,985,669, Krummel, et al, Oct. 12, 1976. Preferred synthetic crystalline aluminosilicate ion exchange materials are available as Zeolite A, Zeolite P (B), Zeolite X and, to whatever extent this differs from Zeolite P, the so-called Zeolite MAP. Natural types, including clinoptilolite, may be used. Zeolite A has the formula: $Na_{12}[(AlO_2)_{12}(SiO_2)_{12}].xH_2O$ wherein x is from 20 to 30, especially 27. Dehydrated zeolites (x=0–10) may also be used. Preferably, the aluminosilicate has a particle size of 0.1–10 microns in diameter.

Detergent builders other than silicates can be used in the compositions herein to assist in controlling mineral hardness. They can be used in conjunction with or instead of aluminosilicates and silicates. Inorganic as well as organic builders can be used. Builders are used in automatic dishwashing to assist in the removal of particulate soils.

Inorganic or non-phosphate-containing detergent builders include, but are not limited to, phosphonates, phytic acid, carbonates (including bicarbonates and sesquicarbonates), sulfates, citrate, zeolite, and aluminosilicates.

Aluminosilicate builders may be used in the present compositions though are not preferred for automatic dishwashing detergents. (See U.S. Pat. No. 4,605,509 for examples of preferred aluminosilicates.) Aluminosilicate builders are of great importance in most currently marketed heavy duty granular detergent compositions, and can also be a significant builder ingredient in liquid detergent formulations. Aluminosilicate builders include those having the empirical formula: $Na_zO.Al_2O_3.xSiO_z.yH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In another embodiment, the crystalline aluminosilicate ion exchange material has the formula: $Na_{12}[(AlO_2)_{12}(SiO_2)_{12}].xH_2O$ wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter. Individual particles can desirably be even smaller than 0.1 micron to further assist kinetics of exchange through maximization of surface area. High surface area also increases utility of aluminosilicates as adsorbents for surfactants, especially in granular compositions. Aggregates of aluminosilicate particles may be useful, a single aggregate having dimensions tailored to minimize segregation in granular compositions, while the aggregate particle remains dispersible to submicron individual particles during the wash. As with other builders such as carbonates, it may be desirable to use zeolites in any physical or morphological form adapted to promote surfactant carrier function, and appropriate particle sizes may be freely selected by the formulator.

Polymeric Soil Release Agent

The compositions according to the present invention may optionally comprise one or more soil release agents. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of the laundry cycle and, thus, serve as an anchor for the hydrophilic segments. This can enable stains occuring subsequent to treatment with the soil release agent to be more easily cleaned in later washing procedures.

If utilized, soil release agents will generally comprise from about 0.01% to about 10% preferably from about 0.1% to about 5%, more preferably from about 0.2% to about 3% by weight, of the composition.

The following, all included herein by reference, describe soil release polymers suitable for us in the present invention. U.S. Pat. No. 5,691,298 Gosselink et al., issued Nov. 25, 1997; U.S. Pat. No. 5,599,782 Pan et al., issued Feb. 4, 1997; U.S. Pat. No. 5,415,807 Gosselink et al., issued May 16, 1995; U.S. Pat. No. 5,182,043 Morrall et al., issued Jan. 26, 1993; U.S. Pat. No. 4,956,447 Gosselink et al., issued Sep. 11, 1990; U.S. Pat. No. 4,976,879 Maldonado et al. issued Dec. 11, 1990; U.S. Pat. No. 4,968,451 Scheibel et al., issued Nov. 6, 1990; U.S. 4,925,577 Borcher, Sr. et al., issued May 15, 1990; U.S. Pat. No. 4,861,512 Gosselink, issued Aug. 29, 1989; U.S. Pat. No. 4,877,896 Maldonado et al., issued Oct. 31, 1989; U.S. 4,702,857 Gosselink et al., issued Oct. 27, 1987; U.S. Pat. No. 4,711,730 Gosselink et al., issued Dec. 8, 1987; U.S. Pat. No. 4,721,580 Gosselink issued Jan. 26, 1988; U.S. 4,000,093 Nicol et al., issued Dec. 28, 1976; U.S. Pat. No. 3,959,230 Hayes, issued May 25, 1976; U.S. Pat. No. 3,893,929 Basadur, issued Jul. 8, 1975; and European Patent Application 0 219 048, published Apr. 22, 1987 by Kud et al.

Further suitable soil release agents are described in U.S. Pat. No. 4,201,824 Voilland et al.; U.S. Pat. No. 4,240,918 Lagasse et al.; U.S. Pat. No. 4,525,524 Tung et al.; U.S. Pat. No. 4,579,681 Ruppert et al.; U.S. Pat. No. 4,220,918; 4,787,989; EP 279,134 A, 1988 to Rhone-Poulenc Chemie; EP 457,205 A to BASF (1991); and DE 2,335,044 to Unilever N. V., 1974; all incorporated herein by reference.

Clay Soil Removal/Anti-redeposition Agents

The compositions of the present invention can also optionally contain water-soluble ethoxylated amines having clay soil removal and antiredeposition properties. Granular compositions which contain these compounds typically contain from about 0.01% to about 10.0% by weight of the water-soluble ethoxylates amines; liquid detergent compositions typically contain about 0.01% to about 5%.

Polymeric Dispersing Agents

Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967.

Acrylic/maleic-based copolymers may also be used as a preferred component of the dispersing anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

Brightener

Any optical brighteners or other brightening or whitening agents known in the art can be incorporated at levels typically from about 0.01% to about 1.2%, by weight, into the detergent compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Artic White CC and Artic White CWD, the 2-(4-styryl-phenyl)-2H-naptho[1,2-d]triazoles; 4,4'-bis-(1,2,3-triazol-2-yl)-stilbenes; 4,4'-bis(styryl) bisphenyls; and the aminocoumarins. Specific examples of these brighteners include 4-methyl-7-diethyl-amino coumarin; 1,2-bis(benzimidazol-2-yl)ethylene; 1,3-diphenyl-pyrazolines; 2,5-bis(benzoxazol-2-yl)thiophene; 2-styryl-naptho[1,2-d]oxazole; and 2-(stilben-4-yl)-2H-naphtho[1,2-d]triazole. See also U.S. Pat. No. 3,646,015, issued Feb. 29, 1972 to Hamilton.

Dye Transfer Inhibiting Agents

The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein contain units having the following structural formula: R—A$_x$—P; wherein P is a polymerizable unit to which an N—O group can be attached or the N—O group can form part of the polymerizable unit or the N—O group can be attached to both units; A is one of the following structures: —NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

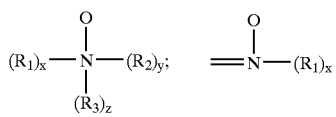

wherein R$_1$, R$_2$, R$_3$ are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa <10, preferably pKa <7, more preferred pKa <6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000. This preferred class of materials can be referred to as "PVNO".

The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., *Chemical Analysis, Vol* 113. "Modern Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The compositions herein may also optionally contain from about 0.005% to 5% by weight of certain types of hydrophilic optical brighteners which also provide a dye transfer inhibition action. If used, the compositions herein will preferably comprise from about 0.01% to 1% by weight of such optical brighteners.

The hydrophilic optical brighteners useful in the present invention are those having the structural formula:

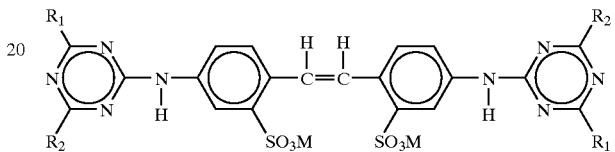

wherein R$_1$ is selected from anilino, N-2-bis-hydroxyethyl and NH-2-hydroxyethyl; R$_2$ is selected from N-2-bis-hydroxyethyl, N-2-hydroxyethyl-N-methylamino, morpholino, chloro and amino; and M is a salt-forming cation such as sodium or potassium.

When in the above formula, R$_1$ is anilino, R$_2$ is N-2-bis-hydroxyethyl and M is a cation such as sodium, the brightener is 4,4'-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX by Ciba-Geigy Corporation. Tinopal-UNPA-GX is the preferred hydrophilic optical brightener useful in the detergent compositions herein.

When in the above formula, R$_1$ is anilino, R$_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX by Ciba-Geigy Corporation.

When in the above formula, R$_1$ is anilino, R$_2$ is morpholino and M is a cation such as sodium, the brightener is 4,4'-bis[(4-anilino-6-morpholino-s-triazine-2-yl)amino]2,2'-stilbenedisulfonic acid, sodium salt. This particular brightener species is commercially marketed under the tradename Tinopal AMS-GX by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal 5BM-GX and/or Tinopal AMS-GX) provides significantly better dye transfer inhibition in aqueous wash solutions than does either of these two granular composition components when used alone. Without being bound by theory, it is believed that such brighteners work this way because they have high affinity for fabrics in the wash solution and therefore deposit relatively quick on these fabrics. The extent to which brighteners deposit on fabrics in the wash solution can be defined by a parameter called the "exhaustion coefficient". The exhaustion coefficient is in general as the ratio of a) the brightener material deposited on fabric to b) the initial brightener concentration in the wash liquor. Brighteners with relatively high exhaustion coefficients are the most suitable for inhibiting dye transfer in the context of the present invention.

Of course, it will be appreciated that other, conventional optical brightener types of compounds can optionally be used in the present compositions to provide conventional fabric "brightness" benefits, rather than a true dye transfer inhibiting effect. Such usage is conventional and well-known to detergent formulations.

Suds Suppressors

Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574 and in front-loading European-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430–447 (John Wiley & Sons, Inc., 1979). One category of suds suppressor of particular interest encompasses monocarboxylic fatty acid and soluble salts therein. See U.S. Pat. No. 2,954,347, issued Sep. 27, 1960 to Wayne St. John. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The compositions herein may also contain non-surfactant suds suppressors. These include, for example: high molecular weight hydrocarbons such as paraffin, fatty acid esters (e.g., fatty acid triglycerides), fatty acid esters of monovalent alcohols, aliphatic $C_{18}$–$C_{40}$ ketones (e.g., stearone), etc. Other suds inhibitors include N-alkylated amino triazines such as tri- to hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 50° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo et al. The hydrocarbons, thus, include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressors are well known in the art and are, for example, disclosed in U.S. Pat. No. 4,265,779, issued May 5, 1981 to Gandolfo at al and EP 0 354 016, published Feb. 7, 1990, by Starch, M. S.

Other silicone suds suppressors are disclosed in U.S. Pat. No. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3,933,672, Bartolotta et al, and in U.S. Pat. No. 4,652,392, Baginski et al, issued Mar. 24, 1987.

An exemplary silicone based suds suppressor for use herein is a suds suppressing amount of a suds controlling agent consisting essentially of:

(i) polydimethylsiloxane fluid having a viscosity of from about 20 cs. to about 1,500 cs. at 25° C.;

(ii) from about 5 to about 50 parts per 100 parts by weight of (i) of siloxane resin composed of $(CH_3)_3SiO_{1/2}$ units of $SiO_2$ units in a ratio of from $(CH_3)_3SiO_{1/2}$ units and to $SiO_2$ units of from about 0.6:1 to about 1.2:1; and (iii) from about 1 to about 20 parts per 100 parts by weight of (i) of a solid silica gel.

In the preferred silicone suds suppressor used herein, the solvent for a continuous phase is made up of certain polyethylene glycols or polyethylene-polypropylene glycol copolymers or mixtures thereof (preferred), or polypropylene glycol. The primary silicone suds suppressor is branched/crosslinked and preferably not linear.

To illustrate this point further, typical liquid laundry detergent compositions with controlled suds will optionally comprise from about 0.001 to about 1, preferably from about 0.01 to about 0.7, most preferably from about 0.05 to about 0.5, weight % of said silicone suds suppressor, which comprises (1) a nonaqueous emulsion of a primary antifoam agent which is a mixture of (a) a polyorganosiloxane, (b) a resinous siloxane or a silicone resin-producing silicone compound, (c) a finely divided filler material, and (d) a catalyst to promote the reaction of mixture components (a), (b) and (c), to form silanolates; (2) at least one nonionic silicone surfactant; and (3) polyethylene glycol or a copolymer of polyethylene-polypropylene glycol having a solubility in water at room temperature of more than about 2 weight %; and without polypropylene glycol. Similar amounts can be used in granular compositions, gels, etc. See also U.S. Pat. No. 4,978,471, Starch, issued Dec. 18, 1990, and U.S. Pat. No. 4,983,316, Starch, issued Jan. 8, 1991, U.S. Pat. No. 5,288,431, Huber et al., issued Feb. 22, 1994, and U.S. Pat. Nos. 4,639,489 and 4,749,740, Aizawa et al at column 1, line 46 through column 4, line 35.

The silicone suds suppressor herein preferably comprises polyethylene glycol and a copolymer of polyethylene glycol/polypropylene glycol, all having an average molecular weight of less than about 1,000, preferably between about 100 and 800. The polyethylene glycol and polyethylenepolypropylene copolymers herein have a solubility in water at room temperature of more than about 2 weight %, preferably more than about 5 weight %.

The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

The preferred silicone suds suppressors used herein do not contain polypropylene glycol, particularly of 4,000 molecular weight. They also preferably do not contain block copolymers of ethylene oxide and propylene oxide, like PLURONIC L101.

Other suds suppressors useful herein comprise the secondary alcohols (e.g., 2-alkyl alkanols) and mixtures of such alcohols with silicone oils, such as the silicones disclosed in U.S. Pat. Nos. 4,798,679, 4,075,118 and EP 150,872. The secondary alcohols include the $C_6$–$C_{16}$ alkyl alcohols having a $C_1$–$C_{16}$ chain. A preferred alcohol is 2-butyl octanol, which is available from Condea under the trademark ISOFOL 12. Mixtures of secondary alcohols are available under the trademark ISALCHEM 123 from Enichem. Mixed suds suppressors typically comprise mixtures of alcohol+silicone at a weight ratio of 1:5 to 5:1.

For any granular compositions to be used in automatic laundry washing machines, suds should not form to the extent that they overflow the washing machine. Suds suppressors, when utilized, are preferably present in a "suds suppressing amount. By "suds suppressing amount" is meant that the formulator of the composition can select an amount of this suds controlling agent that will sufficiently control the suds to result in a low-sudsing granular detergent for use in automatic laundry washing machines.

The compositions herein may comprise from 0% to about 10% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%–3% by weight of the finished compositions.

Alkoxylated Polycarboxylates

Alkoxylated polycarboxylates such as those prepared from polyacrylates are useful herein to provide additional grease removal performance. Such materials are described in WO 91/08281 and PCT 90/01815 at p. 4 et seq., incorporated herein by reference. Chemically, these materials comprise polyacrylates having one ethoxy side-chain per every 7–8 acrylate units. The side-chains are of the formula —$(CH_2CH_2O)_m(CH_2)_nCH_3$ wherein m is 2–3 and n is 6–12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Fabric Softeners

Various through-the-wash fabric softeners, especially the impalpable smectite clays of U.S. Pat. No. 4,062,647, Storm and Nirschl, issued Dec. 13, 1977, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 4,375,416, Crisp et al, Mar. 1, 1983 and U.S. Pat. No. 4,291,071, Harris et al, issued Sep. 22, 1981.

The compositions of the present invention may be of an physical form , depending upon the end use of the composition. Typically, the compositions of the present invention may be in the form of liquid, liquid-gel, gel, thixatropic gel, powder, granule (such as, high bulk density granules, or the so-called "fluffy" granules), paste, tablet, bar and the like.

Similarly, the compositions of the present invention can be used in a variety of different applications. Such compositions would include, hard surface cleaniners, bleaches, automatic dishwashing, LDL's, HDL's (both aqueous and non-aqueous), heavy duty laundry compositions, laundry-pretreaters, shampoos, personal cleansers and the like. The compositions of the present invention are especially suitable for use in automatic dishwashing, bleaches and HDL compositions.

The compositions of the present invention may be in the form of a personal cleansing compositions or shampoos. Typically these compositions contain a shampoo composition adjunct ingredient which is preferably selected from anti-dandruf agents (preferably platelet pyridinethione salt crystals, sulfur, octopirox, selenium sulfide, ketoconazole and pyridinethione salts), co-surfactants (preferably selected from anionic surfactant, nonionic surfactant, cationic surfactant, amphoteric surfactant, zwitterionic surfactants, and mixtures thereof), silicone hair conditioning agent, polyalkylene glycols, suspending agent, water, water soluble cationic polymeric conditioning agents, hydrocarbon conditioning agents, foam boosters, preservatives, thickeners, cosurfactants, dyes, perfumes, solvents, styling polymers, anti-static agents, deposition polymers, styling polymers and solvent, dispersed phase polymers, non-volatile hydrocarbons conditioning agents, silicone conditioning agents, suspending agent, cationic spreading agents, phase separation initiators, and pediculocides and mixtures thereof. These and other suitable materials for incorporation into the shampoo compositions can be found in WO 99/18929 and WO 99/18928.

The compositions of the present invention can also be in the form of LDL compositions. These LDL compositions include, in addition to those detailed previously, additives typically used in LDL formulations, such as diamines, divalent ions, suds boosting polymers, soil release polymers, polymeric dispersants, polysaccharides, abrasives, bactericides, tarnish inhibitors, builders, enzymes, dyes, perfumes, thickeners, antioxidants, processing aids, suds boosters, buffers, antifungal or mildew control agents, insect repellants, anti-corrosive aids, and chelants.

The compositions of the present invention may be in the form of a non-aqueous, liquid, heavy-duty detergent compositions in the form of a stable suspension of solid, substantially insoluble particulate material dispersed throughout a structured, surfactant-containing liquid phase.

Suitable types of non-aqueous surfactant liquids which can be used to form the liquid phase of the compositions herein include the alkoxylated alcohols, ethylene oxide (EO)-propylene oxide (PO) block polymers, polyhydroxy fatty acid amides, alkylpolysaccharides, and the like.

The liquid phase of the HDL compositions herein may also comprise one or more non-surfactant, non-aqueous organic solvents. Suitable types of low-polarity solvents useful in the non-aqueous liquid detergent compositions herein do include non-vicinal $C_4$–$C_8$ alkylene glycols, alkylene glycol mono lower alkyl ethers, lower molecular weight polyethylene glycols, lower molecular weight methyl esters and amides, and the like. Mixtures of non-surfactant, non-aqueous organic solvents and non-aqueous surfactant liquids are also contemplated.

The non-aqueous liquid phase of the HDL compositions of this invention is prepared by combining with the non-aqueous organic liquid diluents hereinbefore described a surfactant which is generally, but not necessarily, selected to add structure to the non-aqueous liquid phase of the detergent compositions herein. Structuring surfactants can be of the anionic, nonionic, cationic, and/or amphoteric types.

The most preferred type of anionic surfactant for use as a structurant in the HDL compositions herein comprises the linear alkyl benzene sulfonate (LAS) surfactants.

The non-aqueous HDL compositions herein preferably comprise a solid phase particulate material which is dispersed and suspended within the liquid phase. Generally such particulate material will range in size from about 0.1 to 1500 microns, more preferably from about 0.1 to 900 microns. Most preferably, such material will range in size from about 5 to 200 microns.

The particulate material utilized herein can comprise one or more types of detergent composition components which in particulate form are substantially insoluble in the non-aqueous liquid phase of the composition. The types of particulate materials which can be utilized are described are peroxygen bleaching agent, organic builder, inorganic alkalinity source (preferably include water-soluble alkali metal carbonates, bicarbonates, borates, pyrophosphates, orthophosphates, polyphosphates phosphonates, silicates and metasilicates), colored speckles and mixtures thereof.

The present invention also comprises aqueous based liquid detergent compositions. The aqueous liquid detergent compositions of the present invention comprise a surfactant system which preferably contains one or more detersive co-surfactants in addition to the branched surfactants disclosed above. The additional co-surfactants can be selected from nonionic detersive surfactant, anionic detersive surfactant, zwitterionic detersive surfactant, amine oxide detersive surfactant, and mixtures thereof. The surfactant system typically comprises from about 5% to about 70%, preferably from about 15% to about 30%, by weight of the detergent composition. These surfactants are hereinbefore described.

In addition to the liquid and solid phase components as hereinbefore described, the aqueous and non-aqueous based detergent compositions can, and preferably will, contain various other optional components. Such optional components may be in either liquid or solid form. The optional components may either dissolve in the liquid phase or may be dispersed within the liquid phase in the form of fine particles or droplets. Suitable optional material includes for example chelating agents, enzymes, builders, bleach catalysts, bleach activators, thickeners, viscosity control agents and/or dispersing agents suds boosters, liquid bleach activator, dye transfer inhibitors solvents, suds suppressors, structure elasticizing agent, anti redeposition agents, to exemplify but a few possible optional ingredients. Some of the materials which may optionally be utilized in the compositions herein are described in greater detail. Further details on suitable adjunct ingredients to HDL compositions, methods of preparing same and use in the compositions can be found in WO 99/19451 and WO 99/19450.

Other Ingredients

The detergent compositions will further preferably comprise one or more detersive adjuncts selected from the following: electrolytes (such as sodium chloride), polysaccharides, abrasives, bactericides, tarnish inhibitors, dyes, antifungal or mildew control agents, insect repellents, perfumes, hydrotropes, thickeners, processing aids, suds boosters, anti-corrosive aids, stabilizers and antioxidants. A wide variety of other ingredients useful in detergent compositions can be included in the compositions herein, including other active ingredients, carriers, hydrotropes, antioxidants, processing aids, dyes or pigments, solvents for liquid formulations, etc. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous.

An antioxidant can be optionally added to the detergent compositions of the present invention. They can be any conventional antioxidant used in detergent compositions, such as 2,6-di-tert-butyl-4-methylphenol (BHT), carbamate, ascorbate, thiosulfate, monoethanolamine(MEA), diethanolamine, triethanolamine, etc. It is preferred that the antioxidant, when present, be present in the composition from about 0.001% to about 5% by weight.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Further, the compositions may optionally comprises a hydrotrope. Suitable hydrotropes include sodium, potassium, ammonium or water-soluble substituted ammonium salts of toluenesulfonic acid, naphthalenesulfonic acid, cumenesulfonic acid, xylenesulfonic acid.

The manufacture of LDL compositions which comprise a non-aqueous carrier medium can be prepared according to the disclosures of U.S. Pat. Nos. 4,753,570; 4,767,558;

4,772,413; 4,889,652; 4,892,673; GB-A-2,158,838; GB-A-2,195,125; GB-A-2,195,649; U.S. Pat. Nos. 4,988,462; 5,266,233; EP-A-225,654 (Jun. 16 1987); EP-A-510,762 (Oct. 28, 1992); EP-A-540,089 (May 5, 1993); EP-A-540, 090 (May 5, 1993); U.S. Pat. No. 4,615,820; EP-A-565,017 (Oct. 13, 1993); EP-A-030,096 (Jun. 10, 1981), incorporated herein by reference. Such compositions can contain various particulate detersive ingredients stably suspended therein. Such non-aqueous compositions thus comprise a LIQUID PHASE and, optionally but preferably, a SOLID PHASE, all as described in more detail hereinafter and in the cited references.

The LDL compositions of this invention can be used to form aqueous washing solutions for use hand dishwashing. Generally, an effective amount of such LDL compositions is added to water to form such aqueous cleaning or soaking solutions. The aqueous solution so formed is then contacted with the dishware, tableware, and cooking utensils.

An effective amount of the LDL compositions herein added to water to form aqueous cleaning solutions can comprise amounts sufficient to form from about 500 to 20,000 ppm of composition in aqueous solution. More preferably, from about 800 to 5,000 ppm of the detergent compositions herein will be provided in aqueous cleaning liquor.

The mean particle size of the components of granular compositions in accordance with the invention should preferably be such that no more that 5% of particles are greater than 1.7 mm in diameter and not more than 5% of particles are less than 0.15 mm in diameter.

The term mean particle size as defined herein is calculated by sieving a sample of the composition into a number of fractions (typically 5 fractions) on a series of Tyler sieves. The weight fractions thereby obtained are plotted against the aperture size of the sieves. The mean particle size is taken to be the aperture size through which 50% by weight of the sample would pass.

The granular laundry compositions in accordance with the present invention typically has a bulk density of from 100 g/liter to 1400 g/liter, more preferably from 300 g/liter to 1200 g/liter, from 650 g/liter to 1000 g/liter.

High Density Detergent Composition Processes

Various means and equipment are available to prepare high density (i.e., greater than about 550, preferably greater than about 650, grams/liter or "g/l"), high solubility, free-flowing, granular detergent compositions according to the present invention. Current commercial practice in the field employs spray-drying towers to manufacture granular laundry detergents which often have a density less than about 500 g/l. In this procedure, an aqueous slurry of various heat-stable ingredients in the final detergent composition are formed into homogeneous granules by passage through a spray-drying tower, using conventional techniques, at temperatures of about 175° C. to about 225° C. However, if spray drying is used as part of the overall process herein, additional or alternative process steps as described hereinafter must be used to obtain the level of density (i.e., >650 g/l) required by modern compact, low dosage detergent products.

For example, spray-dried granules from a tower can be densified further by loading a liquid such as water or a nonionic surfactant into the pores of the granules and/or subjecting them to one or more high speed mixer/densifiers. A suitable high speed mixer/densifier for this process is a device marketed under the tradename "Lödige CB 30" or "Lödige CB 30 Recycler" which comprises a static cylindrical mixing drum having a central rotating shaft with mixing/cutting blades mounted thereon. In use, the ingredients for the detergent composition are introduced into the drum and the shaft/blade assembly is rotated at speeds in the range of 100–2500 rpm to provide thorough mixing/densification. See Jacobs et al, U.S. Pat. No. 5,149,455, issued Sep. 22, 1992, and U.S. Pat. No. 5,565,422, issued Oct. 15, 1996 to Del Greco et al. Other such apparatus includes the devices marketed under the tradename "Shugi Granulator" and under the tradename "Drais K-TTP 80).

Another process step which can be used to densify further spray-dried granules involves treating the spray-dried granules in a moderate speed mixer/densifier. Equipment such as that marketed under the tradename "Lödige KM" (Series 300 or 600) or "Lödige Ploughshare" mixer/densifiers are suitable for this process step. Such equipment is typically operated at 40–160 rpm. The residence time of the detergent ingredients in the moderate speed mixer/densifier is from about 0.1 to 12 minutes conveniently measured by dividing the steady state mixer/densifier weight by the throughput (e.g., Kg/hr). Other useful equipment includes the device which is available under the tradename "Drais K-T 160". This process step which employs a moderate speed mixer/densifier (e.g. Lödige KM) can be used by itself or sequentially with the aforementioned high speed mixer/densifier (e.g. Lödige CB) to achieve the desired density. Other types of granules manufacturing apparatus useful herein include the apparatus disclosed in U.S. Pat. No. 2,306,898, to G. L. Heller, Dec. 29, 1942.

While it may be more suitable to use the high speed mixer/densifier followed by the low speed mixer/densifier, the reverse sequential mixer/densifier configuration also can be used. One or a combination of various parameters including residence times in the mixer/densifiers, operating temperatures of the equipment, temperature and/or composition of the granules, the use of adjunct ingredients such as liquid binders and flow aids, can be used to optimize densification of the spray-dried granules in the process of the invention. By way of example, see the processes in Appel et al, U.S. Pat. No. 5,133,924, issued Jul. 28, 1992; Delwel et al, U.S. Pat. No. 4,637,891, issued Jan. 20, 1987; Kruse et al, U.S. Pat. No. 4,726,908, issued Feb. 23, 1988; and, Bortolotti et al, U.S. Pat. No. 5,160,657, issued Nov. 3, 1992.

In those situations in which particularly heat sensitive or highly volatile detergent ingredients are to be incorporated into the final detergent composition, processes which do not include spray drying towers are preferred. The formulator can eliminate the spray-drying step by feeding, in either a continuous or batch mode, starting detergent ingredients directly into mixing equipment that is commercially available. One particularly preferred embodiment involves charging a surfactant paste and an anhydrous material into a high speed mixer/densifier (e.g. Lödige CB) followed by a moderate speed mixer/densifier (e.g. Lödige KM) to form high density detergent agglomerates. See Capeci et al, U.S. Pat. No. 5,366,652, issued Nov. 22, 1994 and Capeci et al, U.S. Pat. No. 5,486,303, issued Jan. 23, 1996. Optionally, the liquid/solids ratio of the starting detergent ingredients in such a process can be selected to obtain high density agglomerates that are more free flowing and crisp. See Capeci et al, U.S. Pat. No. 5,565,137, issued Oct. 15, 1996.

Optionally, the process may include one or more recycle streams of undersized particles produced by the process which are fed back to the mixer/densifiers for further agglomeration or build-up. The oversized particles produced by this process can be sent to grinding apparatus and then fed back to the mixing/densifying equipment. These additional recycle process steps facilitate build-up agglomeration of the starting detergent ingredients resulting in a finished composition having a uniform distribution of the desired particle size (400–700 microns) and density (>550 g/l). See Capeci et al, U.S. Pat. No. 5,516,448, issued May 14, 1996 and Capeci et al, U.S. Pat. No. 5,489,392, issued Feb. 6, 1996. Other suitable processes which do not call for the use of spray-drying towers are described by Bollier et al, U.S. Pat. No. 4,828,721, issued May 9, 1989; Beerse et al, U.S. Pat. No. 5,108,646, issued Apr. 28, 1992; and, Jolicoeur, U.S. Pat. No. 5,178,798, issued Jan. 12, 1993.

In yet another embodiment, a high density detergent composition using a fluidized bed mixer. In this process, the various ingredients of the finished composition are combined in an aqueous slurry (typically 80% solids content) and sprayed into a fluidized bed to provide the finished detergent granules. Prior to the fluidized bed, this process can optionally include the step of mixing the slurry using the aforementioned Lödige CB mixer/densifier or a "Flexomix 160" mixer/densifier, available from Shugi. Fluidized bed or moving beds of the type available under the tradename "Escher Wyss" can be used in such processes.

Another suitable process which can be used herein involves feeding a liquid acid precursor of an anionic surfactant, an alkaline inorganic material (e.g. sodium carbonate) and optionally other detergent ingredients into a high speed mixer/densifier so as to form particles containing a partially or totally neutralized anionic surfactant salt and the other starting detergent ingredients. Optionally, the contents in the high speed mixer/densifier can be sent to a moderate speed mixer/densifier (e.g. Lödige KM) for further mixing resulting in the finished high density detergent composition. See Appel et al, U.S. Pat. No. 5,164,108, issued Nov. 17, 1992.

Optionally, high density detergent compositions according to the invention can be produced by blending conventional or densified spray-dried detergent granules with detergent agglomerates in various proportions (e.g. a 60:40 weight ratio of granules to agglomerates) produced by one or a combination of the processes discussed herein. See U.S. Pat. No. 5,569,645, issued Oct. 29, 1996 to Dinniwell et al. Additional adjunct ingredients such as enzymes, perfumes, brighteners and the like can be sprayed or admixed with the agglomerates, granules or mixtures thereof produced by the processes discussed herein.

Laundry Washing Method

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is here meant from 40 g to 300 g of product dissolved or dispersed in a wash solution of volume from 5 to 65 liters, as are typical product dosages and wash solution volumes commonly employed in conventional machine laundry methods.

As noted, surfactants are used herein in detergent compositions, preferably in combination with other detersive surfactants, at levels which are effective for achieving at least a directional improvement in cleaning performance. In the context of a fabric laundry composition, such "usage levels" can vary widely, depending not only on the type and severity of the soils and stains, but also on the wash water temperature, the volume of wash water and the type of washing machine.

Packaging for the Compositions

Commercially marketed executions of the compositions can be packaged in any suitable container including those constructed from paper, cardboard, plastic materials and any suitable laminates. A preferred packaging execution is described in WO 95/02681.

The compositions herein may be packaged in a variety of suitable detergent packaging known to those skilled in the art. The liquid compositions are preferably packaged in conventional detergent plastic bottles.

The following examples are illustrative of the present invention, but are not meant to limit or otherwise define its scope. All parts, percentages and ratios used herein are expressed as percent weight unless otherwise specified.

EXAMPLES

Example 1

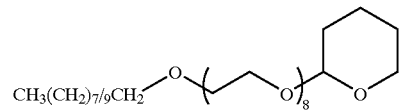

Preparation of $C_{9/11}H_{19/23}O(C_2H_4O)_8$-pyranyl acetal

Neodol 91-8 (50.00 g, 97.9 mmol) is placed into a 1000 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (500 ml), 3,4-dihydro-2H-pyran (24.71 g, 293.7 mmol) and pyridinium p-toluenesulfonate (2.46 g, 9.8 mmol) are added. The mixture is stirred 18 h at ambient and washed twice with saturated sodium bicarbonate. The organic layer is dried with magnesium sulfate, concentrated by rotary evaporation and further dried under vacuum to yield a nearly colorless liquid.

Example 2

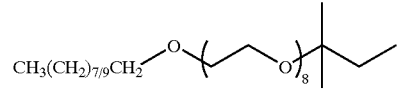

Preparation of $C_{9/11}H_{19/23}O(C_2H_4O)_8$-tert-amyl acetal from tert-amyl alcohol Methylene chloride (300 ml) and magnesium sulfate (47.14 g, 391.6 mmol) are placed into a 1000 ml single-necked round-bottomed flask fitted with a magnetic stirrer. To the vigorously stirring solution is added concentrated sulfuric acid (9.60 g, 97.9 mmol). After stirring for 15 minutes, a solution of t-amyl alcohol (43.15 g, 489.5 mmol) and Neodol 91-8 (50.00 g, 97.9 mmol) in methylene chloride (100 ml) is added. The flask is stoppered tightly and stirred at ambient for 5 days. After transferring the mixture to a 4 L Erlenmeyer flask, 5% sodium bicarbonate solution (750 ml) is carefully added and the mixture stirred until all of the magnesium sulfate is dissolved. This mixture is transferred to a 4 L separatory funnel and is washed twice with brine. The organic layer is dried with magnesium sulfate, concentrated by rotary evaporation and further dried under vacuum to yield a yellow-gold liquid.

Example 3

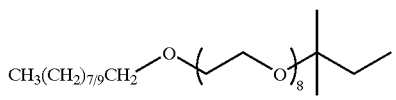

Preparation of $C_{9/11}H_{19/23}O(C_2H_4O)_8$-tert-amyl acetal from 2-methyl-1-butene Neodol 91-8 (109.22 g, 213.9 mmol) is placed into a 1000 ml three-necked round-bottomed flask, fitted with a heating mantle, magnetic stirrer, internal thermometer and argon inlet, and dried under vacuum at 75° C. After cooling to ambient and releasing the vacuum with argon, methylene chloride (225 ml) and 2-methyl-1-butene (75.00 g, 1069.3 mmol) are added. Then boron trifluoride diethyl etherate (7.59 g, 53.5 mmol) is added all at once. This mixture is stirred 5 days at ambient. The mixture is neutralized to a pH of 8–10 with 28% ammonium hydroxide, dried under magnesium sulfate and concentrated by rotary evaporation. After adding 400 ml anhydrous tetrahydrofuran, sulfur trioxide pyridine complex (17.02 g, 106.9 mmol) is added and the mixture sulfated at ambient with stirring for 24 h. After filtering the solids, the filtrate is neutralized to a pH of 8–10 with 25% $NaOCH_3$ in methanol and concentrated by rotary evaporation. This mixture is purified by flash chromatography (5:95 $MeOH:CH_2Cl_2$) and dried under vacuum to yield a yellow-gold liquid.

Example 4

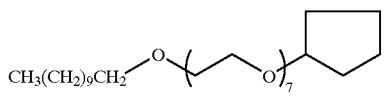

Preparation of $C_{11}H_{23}O(C_2H_4O)_8$-furanyl acetal

Neodol 1-7 (100.00 g, 207.9 mmol) is placed into a 1000 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (500 ml), 2,3-dihydrofuran (43.72 g, 623.7 mmol) and pyridinium p-toluenesulfonate (5.22 g, 20.8 mmol) are added. The mixture is stirred 18 h at ambient and washed twice with saturated sodium bicarbonate. The organic layer is dried with magnesium sulfate, concentrated by rotary evaporation and further dried under vacuum to yield a colorless liquid.

Example 5

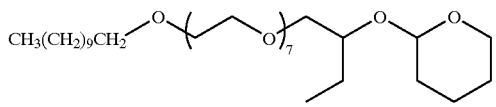

Preparation of $C_{11}H_{23}O(C_2H_4O)_7(C_4H_8O)$-pyranyl acetal

Neodol 1-7 (31.22 g, 64.9 mmol) is placed into a 250 ml three-necked round-bottomed flask, fitted with a heating mantle, magnetic stirrer, internal thermometer and argon inlet and dried under vacuum at 75° C. After releasing the vacuum with argon, sodium metal (0.07 g, 3.2 mmol) is added and the mixture stirred for 1 h at 120° C. After increasing the reaction temperature to 140° C., 1,2-epoxybutane (4.68 g, 64.9 mmol) is added dropwise over 30 minutes. After the addition is complete the mixture is stirred for an additional 1 h at 140° C. The solution is cooled to 90° C. and neutralized with concentrated HCl. After removing water and the last traces of 1,2-epoxybutane under vacuum and cooling to ambient, to the intermediate (20.00 g, 36.2 mmol) is added 3,4-dihydro-2H-pyran (9.13 g, 108.5 mmol), methylene chloride (100 ml) and and pyridinium p-toluenesulfonate (0.91 g, 3.6 mmol). The mixture is stirred 18 h at ambient and then washed twice with saturated sodium bicarbonate. The organic layer is dried with magnesium sulfate, concentrated by rotary evaporation and further dried under vacuum to yield a yellow liquid.

Example 6

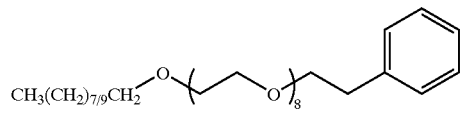

Preparation of $C_{9/11}H_{19/23}O(C_2H_4O)_8$-phenethyl acetal

A Shlenk flask is charged with $CsOH.H_2O$ (329 mg, 1.96 mmol). 1-methyl-2-pyrrolidinone (10 ml), Neodol 91-8 (5.01 g, 9.8 mmol) and phenylacetylene (1.00 g, 9.8 mmol) are successively added. The reaction mixture is vigorously stirred and heated to 100° C. for 12 h. After cooling to ambient, the solution is poured into brine and washed with ether. The combined etheral layer is extracted with water, dried with magnesium sulfate, concentrated by rotary evaporation and then dried under vacuum to yield a yellow liquid. The intermediate is hydrogenated to yield the desired product.

Example 7

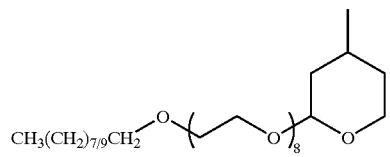

Preparation of $C_{9/11}H_{19/23}O(C_2H_4O)_8$-4-methylpyranyl acetal

The procedure of Example 1 is repeated with the substitution of 3,4-dihydro-4-methyl-2H-pyran for 3,4-dihydro-2H-pyran.

Example 8

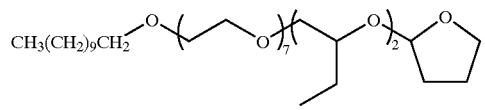

Preparation of $C_{11}H_{23}O(C_2H_4O)_7(C_4H_8O)2$-furanyl acetal

Neodol 1-7 (200.00 g, 415.8 mmol) is placed into a 500 ml three-necked round-bottomed flask, fitted with a heating mantle, magnetic stirrer, internal thermometer and argon inlet and dried under vacuum at 75° C. After releasing the vacuum with argon, sodium metal (0.48 g, 20.8 mmol) is added and the mixture stirred for 1 h at 120° C. After increasing the reaction temperature to 140° C., 1,2-epoxybutane (59.97 g, 831.6 mmol) is added dropwise over 30 minutes. After the addition is complete the mixture is stirred for an additional 1 h at 140° C. The solution is cooled to 90° C. and neutralized with concentrated HCl. After removing water and the last traces of 1,2-epoxybutane under vacuum and cooling to ambient, to the BO capped product (50.00 g, 80.0 mmol) is added 2,3-dihydrofuran (16.82 g, 240.0 mmol), methylene chloride (250 ml) and and pyridinium p-toluenesulfonate (2.01 g, 8.0 mmol). The mixture is stirred 18 h at ambient and then washed twice with saturated sodium bicarbonate. The organic layer is dried with magnesium sulfate, concentrated by rotary evaporation and further dried under vacuum to yield a yellow liquid.

Example 9

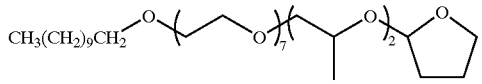

Preparation of $C_{11}H_{23}O(C_2H_4O)_7(C_3H_6O)$-furanyl acetal

The procedure of Example 8 is repeated with the substitution of propylene oxide for 1,2-epoxybutane.

The following examples are illustrative of the present invention, but are not meant to limit or otherwise define its scope. All parts, percentages and ratios used herein are expressed as percent weight unless otherwise specified.

In the following Examples, the abbreviations for the various ingredients used for the compositions have the following meanings.

| | |
|---|---|
| LAS | Sodium linear $C_{12}$ alkyl benzene sulfonate |
| $MBAS_X$ | Mid-chain branched primary alkyl (average total carbons = x) sulfate |
| $MBAE_XS_Z$ | Mid-chain branched primary alkyl (average total carbons = z) ethoxylate (average EO = x) sulfate, sodium salt |
| $MBAE_X$ | Mid-chain branched primary alkyl (average total carbons = x) ethoxylate (average EO = 8) |
| TFAA | C16–18 alkyl N-methyl glucamide |
| CxyEzS | Sodium $C_{1x}$–$C_{1y}$ branched alkyl sulfate condensed with z moles of ethylene oxide |
| CxyFA | $C_{1x}$–$C_{1y}$ fatty acid |
| CxyEz | A $C_{1x-1y}$ branched primary alcohol condensed with an average of z moles of ethylene oxide |
| C24 N-Me Glucamide | $C_{12}$–$C_{14}$ N-methyl glucamide |
| CxAPA | Alkyl amido propyl amine |
| Citric acid | Anhydrous citric acid |
| Carbonate | Anhydrous sodium carbonate with a particle size between 200 $\mu$m and 900 $\mu$m |
| Citrate | Tri-sodium citrate dihydrate of activity 86.4% with a particle size distribution between 425 $\mu$m and 850 $\mu$m |
| Protease | Proteolytic enzyme of activity 4 KNPU/g sold by NOVO Industries A/S under the tradename Savinase |
| Cellulase | Cellulytic enzyme of activity 1000 CEVU/g sold by NOVO Industries A/S under the tradename Carezyme |
| Amylase | Amylolytic enzyme of activity 60 KNU/g sold by NOVO Industries A/S under the tradename Termamyl 60T |
| Lipase | Lipolytic enzyme of activity 100 kLU/g sold by NOVO Industries A/S under the tradename Lipolase |
| Endolase | Endoglunase enzyme of activity 3000 CEVU/g sold by NOVO Industries A/S |
| PB1 | Anhydrous sodium perborate bleach of nominal formula $NaBO_2.H_2O_2$ |
| NOBS | Nonanoyloxybenzene sulfonate in the form of the sodium salt. |
| DTPMP | Diethylene triamine penta (methylene phosphonate), marketed by Monsanto under the Trade name Dequest 2060 |
| MEA | Monoethanolamine |
| PG | Propanediol |
| EtOH | Ethanol |
| Brightener 1 | Disodium 4,4'-bis(2-sulphostyryl)biphenyl |
| Brightener 2 | Disodium 4,4'-bis(4-anilino-6-morpholino-1.3.5-triazin-2-yl)amino)stilbene-2:2'-disulfonate. |
| Silicone antifoam | Polydimethylsiloxane foam controller with siloxane-oxyalkylene copolymer as dispersing agent with a ratio of said foam controller to said dispersing agent of 10:1 to 100:1. |
| NaOH | Solution of sodium hydroxide |
| DTPA | Diethylene triamine pentaacetic acid |
| NaTS | Sodium toluene sulfonic acid |
| Fatty Acid (C12/14) | C12–C14 fatty acid |
| Fatty Acid (TPK) | Topped palm kernel fatty acid |
| Fatty Acid (RPS) | Rapeseed fatty acid |
| Borax | Na tetraborate decahydrate |
| PAA | Polyacrylic Acid (mw = 4500) |
| PEG | Polyethylene glycol (mw = 4600) |
| MES | Alkyl methyl ester sulfonate |
| SAS | Secondary alkyl sulfate |
| NaPS | Sodium paraffin sulfonate |
| C45AS | Sodium $C_{14}$–$C_{15}$ linear alkyl sulfate |
| CxyAS | Sodium $C_{1x}$–$C_{1y}$ alkyl sulfate (or other salt if specified) |
| AQA | $R_2.N^+(CH_3)_x((C_2H_4O)yH)z$ with $R_2 = C_8 - C_{18}$ = where $x + z = 3$, $x = 0$ to 3, $z = 0$ to 3, $y = 1$ to 15. |

-continued

| | |
|---|---|
| STPP | Anhydrous sodium tripolyphosphate |
| Zeolite A | Hydrated Sodium Aluminosilicate of formula $Na_{12}(AlO_2SiO_2)_{12}\cdot 27H_2O$ having a primary particle size in the range from 0.1 to 10 micrometers |
| NaSKS-6 | Crystalline layered silicate of formula $\delta\text{-}Na_2Si_2O_5$ |
| Bicarbonate | Anhydrous sodium bicarbonate with a particle size distribution between 400 $\mu$m and 1200 $\mu$m |
| Silicate | Amorphous Sodium Silicate ($SiO_2:Na_2O$; 2.0 ratio) |
| Sulfate | Anhydrous sodium sulfate |
| PAE | ethoxylated tetraethylene pentamine |
| PIE | ethoxylated polyethylene imine |
| PAEC | methyl quaternized ethoxylated dihexylene triamine |
| MA/AA | Copolymer of 1:4 maleic/acrylic acid, average molecular weight about 70,000. |
| CMC | Sodium carboxymethyl cellulose |
| Protease | Proteolytic enzyme of activity 4 KNPU/g sold by NOVO Industries A/S under the tradename Savinase |
| Cellulase | Cellulytic enzyme of activity 1000 CEVU/g sold by NOVO Industries A/S under the tradename Carezyme |
| Amylase | Amylolytic enzyme of activity 60 KNU/g sold by NOVO Industries A/S under the tradename Termamyl 60T |
| Lipase | Lipolytic enzyme of activity 100 kLU/g sold by NOVO Industries A/S under the tradename Lipolase |
| Percarbonate | Sodium Percarbonate of nominal formula $2Na_2CO_3\cdot 3H_2O_2$ |
| NaDCC | Sodium dichloroisocyanurate |
| TAED | Tetraacetylethylenediamine |
| DTPMP | Diethylene triamine penta (methylene phosphonate), marketed by Monsanto under Tradename Dequest 2060 |
| Photoactivated bleach | Sulfonated Zinc Phthalocyanine bleach encapsulated in dextrin soluble polymer |
| HEDP | 1,1-hydroxyethane diphosphonic acid |
| SRP 1 | Sulfobenzoyl end capped esters with oxyethylene oxy and terephthaloyl backbone |
| SRP 2 | sulfonated ethoxylated terephthalate polymer |
| SRP 3 | methyl capped ethoxylated terephthalate polymer |
| Isofol 16 | Condea trademark for C16 (average) Guerbet alcohols |
| CaCl2 | Calcium chloride |
| MgCl2 | Magnesium chloride |
| DTPA | Diethylene triamine pentaacetic acid |

Examples 10A to 10E

Nonaqueous Liquid Laundry Detergent Compositions

Non-limiting examples of bleach-containing nonaqueous liquid laundry detergent are prepared as follows.

Preparation of LAS Powder for Use as a Structurant

Sodium $C_{12}$ linear alkyl benzene sulfonate (NaLAS) is processed into a powder containing two phases. One of these phases is soluble in the non-aqueous liquid detergent compositions herein and the other phase is insoluble. It is the insoluble fraction which serves to add structure and particle suspending capability to the non-aqueous phase of the compositions herein.

NaLAS powder is produced by taking a slurry of NaLAS in water (approximately 40–50% active) combined with dissolved sodium sulfate (3–15%) and hydrotrope, sodium sulfosuccinate (1–3%). The hydrotrope and sulfate are used to improve the characteristics of the dry powder. A drum dryer is used to dry the slurry into a flake. When the NaLAS is dried with the sodium sulfate, two distinct phases are created within the flake. The insoluble phase creates a network structure of aggregate small particles (0.4–2 um) which allows the finished non-aqueous detergent product to stably suspend solids.

The NaLAS powder prepared according to this example has the following makeup shown in Table I.

TABLE I

| LAS Powder | |
|---|---|
| Component | Wt. % |
| NaLAS | 85% |
| Sulfate | 11% |
| Sulfosuccinate | 2% |
| Water | 2.5% |
| Unreacted, etc. | balance to 100% |
| % insoluble LAS | 17% |
| # of phase (via X-ray diffraction) | 2 |

Non-aqueous based heavy duty liquid laundry detergent compositions which comprise the capped nonionic surfactants of the present invention are presented below.

| Component | A | B | C | D | E |
|---|---|---|---|---|---|
| LAS, From Example 1 | 15 | 15 | 15 | 15 | 5 |
| Nonionic from example 1 | 21.5 | 15 | — | 5 | — |
| Nonionic from example 3 | — | — | — | — | 25 |
| Nonionic from example 4 | — | — | 10 | 5 | — |
| C12,13EO5 | — | 6.5 | 11.5 | 16.5 | 6.5 |
| BPP | 19.5 | 19 | 19 | 19 | 19 |
| Sodium citrate dihydrate | 7 | 7 | 7 | 7 | 7 |
| Bleach activator | 6 | 6 | 6 | 6 | 6 |
| Sodium carbonate | 9 | 9 | 9 | 9 | 9 |
| Maleic-acrylic copolymer | 3 | 3 | 3 | 3 | 3 |
| Colored speckles | 0.4 | 0.4 | 0.4 | 0.4 | 0.4 |

-continued

| Component | A | B | C | D | E |
|---|---|---|---|---|---|
| EDDS | 1 | 1 | 1 | 1 | 1 |
| Cellulase Prills | 0.1 | 0.1 | 0.1 | 0.1 | 0.1 |
| Amylase Prills | 0.4 | 0.4 | 0.4 | 0.4 | 0.4 |
| Ethoxylated diamine quat | 1.3 | 1.3 | 1.3 | 1.3 | 1.3 |
| Sodium Perborate | 12 | 12 | 12 | 12 | 12 |
| Optionals including: | balance | balance | balance | balance | balance |
| brightener, colorant, perfume, thickener, suds suppressor, colored speckles etc. | | | | | |
| | 100% | 100% | 100% | 100% | 100% |

The resulting compositions are stable, anhydrous heavy-duty liquid laundry detergents which provide excellent rates of mixing with water as well as good stain and soil removal performance when used in normal fabric laundering operations.

Example 11

Hand Dishwashing Liquid Compositions

The following Examples further illustrates the invention herein with respect to a hand dishwashing liquid.

EXAMPLE 11

| Ingredient | % (wt.) | Range (% wt.) |
|---|---|---|
| Nonionic from example 2 | 5.0 | 1–20 |
| $MBAE_2S_{15}$ | 2.0 | 0.5–10 |
| Ammonium $C_{12-13}$ alkyl sulfate | 7.0 | 2–35 |
| $C_{12}$–$C_{14}$ ethoxy (1) sulfate | 20.5 | 5–35 |
| Coconut amine oxide | 2.6 | 2–5 |
| Betaine/Tetronic 704 ®** | 0.87–0.10 | 0–2 (mix) |
| Alcohol Ethoxylate $C_{9-11}E_9$ | 1.0 | 0.5–10 |
| Ammonium xylene sulfonate | 4.0 | 1–6 |
| Ethanol | 4.0 | 0–7 |
| Ammonium citrate | 0.06 | 0–1.0 |
| Magnesium chloride | 3.3 | 0–4.0 |
| Calcium chloride | 2.5 | 0–4.0 |
| Ammonium sulfate | 0.08 | 0–4.0 |
| Perfume | 0.18 | 0–0.5 |
| Maxalase ® protease | 0.50 | 0–1.0 |
| Water and minors | Balance | |

**Cocoalkyl betaine.

Examples 10 to 14

Shampoo Compositions

| | Example Number | | | | |
|---|---|---|---|---|---|
| Component | 12 | 13 | 14 | 15 | 16 |
| Ammonium laureth-2 sulfate | 5 | 3 | 2 | 10 | 8 |
| Ammonium lauryl sulfate | 5 | 5 | 4 | 5 | 8 |
| Nonionic from example 3 | 2 | 0 | 0 | 4 | 7 |
| Nonionic from example 6 | 0 | 3 | 0 | 0 | 0 |
| Nonionic from example 9 | 0 | 0 | 4 | 1 | 0 |
| Cocamide MEA | 0 | 0.68 | 0.68 | 0.8 | 0 |
| PEG 14M | 0.1 | 0.35 | 0.5 | 0.1 | 0 |
| Cocoamidopropylbetaine | 2.5 | 2.5 | 0 | 0 | 1.5 |
| Cetylalcohol | 0.42 | 0.42 | 0.42 | 0.5 | 0.5 |
| Stearylalcohol | 0.18 | 0.18 | 0.18 | 0.2 | 0.18 |
| Ethylene glycol distearate | 1.5 | 1.5 | 1.5 | 1.5 | 1.5 |
| Dimethicone[1] | 1.75 | 1.75 | 1.75 | 1.75 | 2.0 |

-continued

| | Example Number | | | | |
|---|---|---|---|---|---|
| Component | 12 | 13 | 14 | 15 | 16 |
| Perfume solution | 0.45 | 0.45 | 0.45 | 0.45 | 0.45 |
| DMDM hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

[1]Dimethicone is a 40 (gum)/60 (fluid) weight ratio blend of SE-76 dimethicone gum available from General Electric Silicones Division and a dimethicone fluid having a viscosity of 350 centistokes.

Examples 17 to 32

Granular Laundry Detergents

The following laundry detergent compositions are prepared in accord with the invention:

| | 17 | 18 | 19 | 20 | 21 | 22 |
|---|---|---|---|---|---|---|
| $MBAS_{14.4}$ | 8.0 | 4.0 | 4.0 | 8.0 | 4.0 | 4.0 |
| C45AS | — | 4.0 | 2.8 | — | 4.0 | 2.8 |
| LAS | — | — | 1.2 | — | — | 1.2 |
| Nonionic from example 4 | — | 3.4 | — | 1.7 | — | — |
| Nonionic from example 1 | 3.4 | — | — | 1.7 | — | 3.4 |
| Nonionic from example 7 | — | — | 3.4 | — | 3.4 | — |
| AQA | 0.4 | 0.5 | 0.6 | 0.8 | 0.8 | 0.8 |
| Zeolite A | 18.1 | 18.1 | 18.1 | 18.1 | 18.1 | 18.1 |
| Carbonate | 13.0 | 13.0 | 13.0 | 27.0 | 27.0 | 27.0 |
| Silicate | 1.4 | 1.4 | 1.4 | 3.0 | 3.0 | 3.0 |
| Sulfate | 26.1 | 26.1 | 26.1 | 26.1 | 26.1 | 26.1 |
| PB4 | 9.0 | 9.0 | 9.0 | 9.0 | 9.0 | 9.0 |
| TAED | 1.5 | 1.5 | 1.5 | 1.5 | 1.5 | 1.5 |
| DTPMP | 0.25 | 0.25 | 0.25 | 0.25 | 0.25 | 0.25 |
| HEDP | 0.3 | 0.3 | 0.3 | 0.3 | 0.3 | 0.3 |
| Protease | 0.26 | 0.26 | 0.26 | 0.26 | 0.26 | 0.26 |
| Amylase | 0.1 | 0.1 | 0.1 | 0.1 | 0.1 | 0.1 |
| MA/AA | 0.3 | 0.3 | 0.3 | 0.3 | 0.3 | 0.3 |
| CMC | 0.2 | 0.2 | 0.2 | 0.2 | 0.2 | 0.2 |
| Photoactivated bleach | 15 ppm | 15 ppm | 15 ppm | 15 ppm | 15 ppm | 15 ppm |
| Brightener 1 | 0.09 | 0.09 | 0.09 | 0.09 | 0.09 | 0.09 |
| Perfume | 0.3 | 0.3 | 0.3 | 0.3 | 0.3 | 0.3 |
| Silicone antifoam | 0.5 | 0.5 | 0.5 | 0.5 | 0.5 | 0.5 |
| Misc/minors to 100% | | | | | | |
| Density in g/litre | 850 | 850 | 850 | 850 | 850 | 850 |

The following laundry detergent compositions are prepared in accord with the invention:

| | 23 | 24 | 25 | 26 | 27 |
|---|---|---|---|---|---|
| MBAS14.4 | 22 | 16.5 | 11 | 1–5.5 | 10–25 |
| Any Combination of: | 0 | 1–5.5 | 11 | 16.5 | 0–5 |
| C45 AS | | | | | |
| C45E1S | | | | | |
| LAS | | | | | |
| C16 SAS | | | | | |
| C14–17 NaPS | | | | | |
| C14–18 MES | | | | | |
| MBAE2S14.3 | | | | | |
| AQA | 2 | 2 | 2 | 2 | 0.5–4 |
| Nonionic from example 2 | — | 1.5 | — | — | 1–4 |
| Nonionic from example 5 | 1.5 | — | — | 1.5 | 1–4 |
| Nonionic from example 1 | — | — | 1.5 | — | 1–4 |

-continued

|  | 23 | 24 | 25 | 26 | 27 |
|---|---|---|---|---|---|
| Zeolite A | 27.8 | 27.8 | 27.8 | 27.8 | 20–30 |
| PAA | 2.3 | 2.3 | 2.3 | 2.3 | 0–5 |
| Carbonate | 27.3 | 27.3 | 27.3 | 27.3 | 20–30 |
| Silicate | 0.6 | 0.6 | 0.6 | 0.6 | 0–2 |
| PB1 | 1.0 | 1.0 | 1.0 | 1.0 | 0–3 |
| Protease | 0–0.5 | 0–0.5 | 0–0.5 | 0–0.5 | 0–0.5 |
| Cellulase | 0–0.3 | 0–0.3 | 0–0.3 | 0–0.3 | 0–0.5 |
| Amylase | 0–0.5 | 0–0.5 | 0–0.5 | 0–0.5 | 0–1 |
| SRP 1 | 0.4 | 0.4 | 0.4 | 0.4 | 0–1 |
| Brightener 1 or 2 | 0.2 | 0.2 | 0.2 | 0.2 | 0–0.3 |
| PEG | 1.6 | 1.6 | 1.6 | 1.6 | 0–2 |
| Sulfate | 5.5 | 5.5 | 5.5 | 5.5 | 0–6 |
| Silicone Antifoam | 0.42 | 0.42 | 0.42 | 0.42 | 0–0.5 |
| Moisture & Minors | | | Balance | | |
| Density (g/L) | 663 | 663 | 663 | 663 | 600–700 |

The following laundry detergent compositions are prepared in accord with the invention:

|  | 28 | 29 | 30 | 31 | 32 |
|---|---|---|---|---|---|
| MBAS14.4 | 16.5 | 12.5 | 8.5 | 4 | 1–25 |
| Any Combination of: | 0–6 | 10 | 14 | 18.5 | 0–20 |
| C45 AS | | | | | |
| C45E1S | | | | | |
| LAS | | | | | |
| C16 SAS | | | | | |
| C14–17 NaPS | | | | | |
| C14–18 MES | | | | | |
| MBAE2S14.3 | | | | | |
| AQA | 2 | 2 | 2 | 2 | 1–4 |
| TFAA | 1.6 | 1.6 | 1.6 | 1.6 | 0–4 |
| Nonionic from example 6 | 5 | — | — | 5 | 1–6 |
| Nonionic from example 4 | — | 5 | — | — | 1–6 |
| Nonionic from example 3 | — | — | 5 | — | 1–6 |
| Zeolite A | 15 | 15 | 15 | 15 | 10–30 |
| NaSKS-6 | 11 | 11 | 11 | 11 | 5–15 |
| Citrate | 3 | 3 | 3 | 3 | 0–8 |
| MA/AA | 4.8 | 4.8 | 4.8 | 4.8 | 0–8 |
| HEDP | 0.5 | 0.5 | 0.5 | 0.5 | 0–1 |
| Carbonate | 8.5 | 8.5 | 8.5 | 8.5 | 0–15 |
| Percarbonate or PB1 | 20.7 | 20.7 | 20.7 | 20.7 | 0–25 |
| TAED | 4.8 | 4.8 | 4.8 | 4.8 | 0–8 |
| Protease | 0.9 | 0.9 | 0.9 | 0.9 | 0–1 |
| Lipase | 0.15 | 0.15 | 0.15 | 0.15 | 0–0.3 |
| Cellulase | 0.26 | 0.26 | 0.26 | 0.26 | 0–0.5 |
| Amylase | 0.36 | 0.36 | 0.36 | 0.36 | 0–0.5 |
| SRP 1 | 0.2 | 0.2 | 0.2 | 0.2 | 0–0.5 |
| Brightener 1 or 2 | 0.2 | 0.2 | 0.2 | 0.2 | 0–0.4 |
| Sulfate | 2.3 | 2.3 | 2.3 | 2.3 | 0–25 |
| Silicone Antifoam |  | 0.4 | 0.4 | 0.4 | 0–1 |
| Moisture & Minors | | | Balance | | |
| Density (g/L) | 850 | 850 |  | 850 | 850 |

Examples 33 to 40

Hard Surface Cleaners

The following compositions were made by mixing the listed ingredients in the listed proportions. These compositions were used neat to clean marble and dilute to clean lacquered wooden floors. Excellent cleaning and surface safety performance was observed.

|  | 33 | 34 | 35 | 36 | 37 | 38 | 39 | 40 |
|---|---|---|---|---|---|---|---|---|
| Nonionic from example 7 | 3.0 | — | 1.0 | — | 3.2 | — | — | — |
| Nonionic from example 1 | — | 3.0 | 2.0 | — | — | — | 4.0 | 8.0 |
| Nonionic from example 9 | — | — | 2.0 | 3.2 | — | 3.2 | 4.0 | — |
| C23E3 | 1.0 | 1.0 | 1.5 | 1.3 | 1.3 | 1.5 | 3.0 | 3.5 |
| C24E21 | 2.0 | 2.0 | 2.5 | 1.9 | 1.9 | 2.0 | 5.0 | 6.0 |
| NaPS | 2.0 | 1.5 | 1.2 | 1.2 | 1.0 | 1.7 | 3.0 | 2.5 |
| NaTS | 1.2 | 3.0 | 2.2 | 2.0 | 2.0 | 1.5 | 4.0 | 5.0 |
| MgSO4 | 0.20 | 0.9 | 0.30 | 0.50 | 1.3 | 2.0 | 1.0 | 3.0 |
| Citrate | 0.3 | 1.0 | 0.5 | 0.75 | 1.8 | 3.0 | 1.5 | 6.0 |
| NaHCO3 | 0.06 | 0.1 | — | 0.1 | — | 0.2 | — | — |
| Na2HPO4 | — | — | 0.1 | — | 0.3 | — | — | — |
| Na2H2P2O7 | — | — | — | — | — | — | 0.2 | 0.5 |
| pH | 8.0 | 7.5 | 7.0 | 7.25 | 8.0 | 7.4 | 7.5 | 7.2 |
| Water and Minors | | | | q.s. to 100% | | | | |

Example 41

Automatic Dishwashing Compositions

|  | Weight % | |
|---|---|---|
| Ingredients: | A | B |
| Sodium Tripolyphosphate (STPP) | 24.0 | 45.0 |
| Sodium Carbonate | 20.0 | 13.5 |
| Hydrated 2.0 r Silicate | 15.0 | 13.5 |
| Nonionic Surfactant[1] | 3.0 | 3.0 |
| $C_{14}$Amine Oxide | 1.0 | 1.0 |
| Polymer[2] | 4.0 | — |
| Protease (4% active) | 0.83 | 0.83 |
| Amylase (0.8% active) | 0.5 | 0.5 |
| Perborate Monohydrate (15.5% active AvO)[3] | 14.5 | 14.5 |
| Cobalt Catalyst[4] | 0.008 | — |
| Dibenzoyl Peroxide (18% active) | 4.4 | 4.4 |
| Water, Sodium Sulfate, Misc. | Balance | Balance |

[1]Nonionic surfactant according to Example 1.
[2]Terpolymer selected from either 60% acrylic acid/20% maleic acid/20% ethyl acrylate, or 70% acrylic acid/10% maleic acid/20% ethyl acrylate.
[3]The AvO level of the above formula is 2.2%.
[4]Pentaamineacetatocobalt(III) nitrate prepared as described hereinbefore; may be replaced by MnTacN.

The following examples further illustrate phosphate built ADD compositions which contain a bleach/enzyme particle, but are not intended to be limiting thereof. These compositions are suitable for use in the methods of the present invention. All percentages noted are by weight of the finished compositions, other than the perborate (monohydrate) component, which is listed as AvO.

EXAMPLES 42–43

|  | Weight % | |
|---|---|---|
| Ingredients: | 42 | 43 |
| STPP | 30.0 | 32.0 |
| $Na_2CO_3$ | 30.5 | 20.5 |
| 2 R Silicate ($SiO_2$) | 8.0 | 4.0 |
| Catalyst[1] | 0.008 | 0.004 |
| Savinase ™ 12T | — | 1.1 |
| Protease D | 0.9 | — |
| Perborate (AvO) | 5.0 | 0.7 |
| Polymer[2] | 4.0 | — |
| Dibenzoyl Peroxide | 0.2 | 0.15 |
| Paraffin | 0.5 | 0.5 |
| Benzotriazole | 0.10 | 0.3 |

EXAMPLES 42–43-continued

| Ingredients: | Weight % | |
|---|---|---|
| | 42 | 43 |
| $C_{14}$Amine Oxide | 0.5 | 0.5 |
| Nonionic Surfactant[3] | 2.0 | 2.0 |
| Sodium Sulfate, Moisture | Balance | |

[1]Pentaamineacetatocobalt(III) nitrate; may be replaced by MnTacN.
[2]Polyacrylate or Acusol 480N or polyacrylate/polymethacrylate copolymers.
[3]Nonionic surfactant according to Example 7.

In compositions of Examples 42 and 43, respectively, the catalyst and enzymes are introduced into the compositions as 200–2400 micron composite particles which are prepared by spray coating, fluidized bed granulation, marumarizing, prilling, or flaking/grinding operations. If desired, the protease and amylase enzymes may be separately formed into their respective catalyst/enzyme composite particles, for reasons of stability, and these separate compositions added to the compositions.

The following example further illustrate ADD granular compositions with chlorine bleach suitable for use in the methods of this present invention.

EXAMPLE 44–45

| Ingredients: | Weight % | |
|---|---|---|
| | 44 | 45 |
| STPP | 25 | 31 |
| $Na_2CO_3$ | 23.0 | 15.0 |
| 2 R Silicate ($SiO_2$) | 17.5 | 25.0 |
| Hypochlorite | 1.0 | 3.0 |
| Polymer[1] | 2.0 | — |
| Dibenzoyl Peroxide | — | 0.15 |
| Paraffin | 1.0 | 1.0 |
| $C_{14}$Amine Oxide | 0.5 | 1.0 |
| Nonionic Surfactant[2] | 2.0 | 3.0 |
| Sodium Sulfate, Moisture | Balance | |

[1]Polyacrylate or Acusol 480N or polyacrylate/polymethacrylate copolymers
[3]Nonionic surfactant according to Example 8.

The following examples further illustrate ADD liquid-gel compositions suitable for use in the methods of this present invention.

EXAMPLES 46–47

| Ingredients: | Weight % | |
|---|---|---|
| | 46 | 47 |
| STPP | 32.0 | 25.0 |
| $Na_2CO_3$ | 0.7 | 2.0 |
| 2 R Silicate ($SiO_2$) | 0.3 | 1.0 |
| Savinase ™ 12T | 2.0 | 1.0 |
| Termamyl ™ | 1.4 | 0.5 |
| Perborate (AvO) | 3.5 | — |
| $C_{16}$ Amine Oxide | 0.8 | 0.8 |
| Nonionic Surfactant[1] | 3.5 | 3.5 |
| Sodium Sulfate, Moisture | Balance | |

[1]Nonionic surfactant according to Example 3.

The following examples further illustrate ADD rinse aid compositions suitable for use in the methods of this present invention.

EXAMPLES 48–49

| Ingredients: | Weight % | |
|---|---|---|
| | 48 | 49 |
| Citric Acid | 10.0 | 15.0 |
| Ethanol | 5.0 | 10.0 |
| HEDP Acid[1] | 1.0 | 0.7 |
| Sodium Cumene Sulfonate | 15.0 | 10.0 |
| Polymer[2] | — | 1.0 |
| $C_{14}$Amine Oxide | 2.0 | 0.5 |
| Nonionic Surfactant[3] | 8.0 | 8.0 |
| Nonionic Surfactant[4] | 6.0 | — |
| Moisture | Balance | |

[1]1-Hydroxyethylidene-1,1-diphoshonic acid
[2]Polyacrylate or Acusol 480N or polyacrylate/polymethacrylate copolymers
[3]Nonionic surfactant according to Example 1.
[4]Nonionic surfactant according to Example 5.

The following examples further illustrate ADD tablet compositions suitable for use in the methods of this present invention.

EXAMPLES 50–51

| Ingredients: | Weight % | |
|---|---|---|
| | 50 | 51 |
| STPP | 48.0 | 30 |
| $Na_2CO_3$ | 15.0 | 25.0 |
| 2 R Silicate ($SiO_2$) | 4.0 | 8.0 |
| Catalyst[1] | 0.008 | 0.004 |
| Savinase ™ 12T | — | 1.0 |
| Termamyl ™ | 0.6 | 0.5 |
| Perborate (AvO) | 10.0 | 15.0 |
| Polymer[2] | 2.0 | 2.0 |
| Dibenzoyl Peroxide | 0.2 | 0.15 |
| Paraffin | 1.0 | 1.0 |
| Benzotriazole | 0.5 | 0.5 |
| $C_{16}$Amine Oxide | 1.0 | 1.0 |
| Nonionic Surfactant[3] | 3.0 | 3.0 |
| Sodium Sulfate, Moisture | Balance | |

[1]Pentaamineacetatocobalt(III) nitrate; may be replaced by MnTacN
[2]Polyacrylate or Acusol 480N or polyacrylate/polymethacrylate copolymers
[3]Nonionic surfactant according to Example 5.

What is claimed is:

1. An ether-capped poly(oxyalkylated) alcohol having the formula:

$$RO(R^1O)_xR^2$$

wherein, R is selected from the group consisting of linear or branched, saturated or unsaturated, substituted or unsubstituted, aliphatic or aromatic hydrocarbon radicals having from about 1 to about 30 carbon atoms; $R_1$ may be the same or different, and is independently selected from the group consisting of branched or linear $C_2$ to $C_7$ alkylene in any given molecule: $R^2$ is selected from the group consisting of:

(i) a 4 to 8 membered substituted, or unsubstituted heterocyclic ring containing from 1 to 3 hetero atoms;

(ii) a 7 to 13 membered substituted, or unsubstituted polycyclic ring;

(iii) a hydrocarbon of the formula:

$$—(CH_2)_y—X$$

wherein, y is an integer from 1 to 7, X is selected from the group consisting of:

(A) a 4 to 8 membered substituted, or unsubstituted, partially unsaturated cyclic hydrocarbon radical;
(B) a 4, 5, 7 or 8 membered substituted or unsubstituted aromatic hydrocarbon radical;
(C) a 6 membered aromatic hydrocarbon radical wherein R is a linear or branched saturated or unsaturated, $C_9$ to $C_{20}$ aliphatic hydrocarbon radical;
(D) an aromatic hydrocarbon selected from the group consisting of:

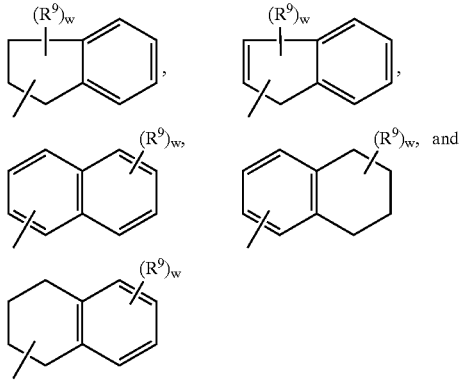

wherein each $R^9$ is independently selected from the group consisting of hydrogen, linear or branched, saturated or unsaturated, substituted or unsubstituted, aliphatic hydrocarbon or alkoxy radical having from about 1 to about 10 carbon atoms, w is an integer from 1 to 3; and
(iv) a hydrocarbon radical of the formula:

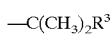

wherein $R^3$ is selected from the group consisting of:
(A) linear or branched, saturated or unsaturated, aliphatic hydrocarbon radical having from about 2 to about 30 carbon atoms;
(B) methyl, wherein R is branched saturated or unsaturated, aliphatic hydrocarbon radical having from 1 to 4 carbon atoms;
(C) a substituted or unsubstituted aromatic hydrocarbon radical having from about 15 to about 30 carbon atoms;
wherein x is a number from 1 to about 30.

2. The compound as claimed in claim 1 wherein R is a linear or branched, saturated or unsaturated, substituted or unsubstituted, aliphatic hydrocarbon radical having from about 1 to about 20 carbon atoms.

3. The compound as claimed in claim 2 wherein R is a linear or branched, saturated, aliphatic hydrocarbon radicals having from about 4 to about 18 carbon atoms.

4. The compound as claimed in claim 1 wherein R has the formula:

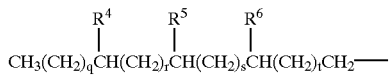

wherein
$R^4$, $R^5$, and $R^6$ are each independently selected from hydrogen, $C_1$–$C_3$ alkyl, and mixtures thereof, provided that $R^4$, $R^5$, and $R^6$ are not all hydrogen and, when t is 0, at least $R^4$ or $R^5$ is not hydrogen; q, r, s, t are each independently integers from 0 to 13.

5. The compound as claimed in claim 4 wherein R has the formula:

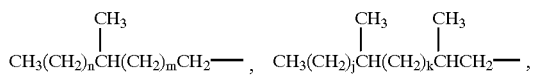

wherein n, m, j and k are each independently integers from 0 to 13.

6. The compound as claimed in claim 1 wherein $R_2$ is a hydrocarbon radical of the formula:

wherein $R^3$ is defined as above.

7. The compound as claimed in claim 6 wherein $R^3$ is $CH_3CH_2$.

8. The compound as claimed in claim 1 wherein $R^2$ is a 4 to 8 member substituted, or unsubstituted heterocyclic ring containing from 1 to 3 hetero atoms.

9. The compound as claimed in claim 8 wherein said heterocyclic is selected from the group consisting of:

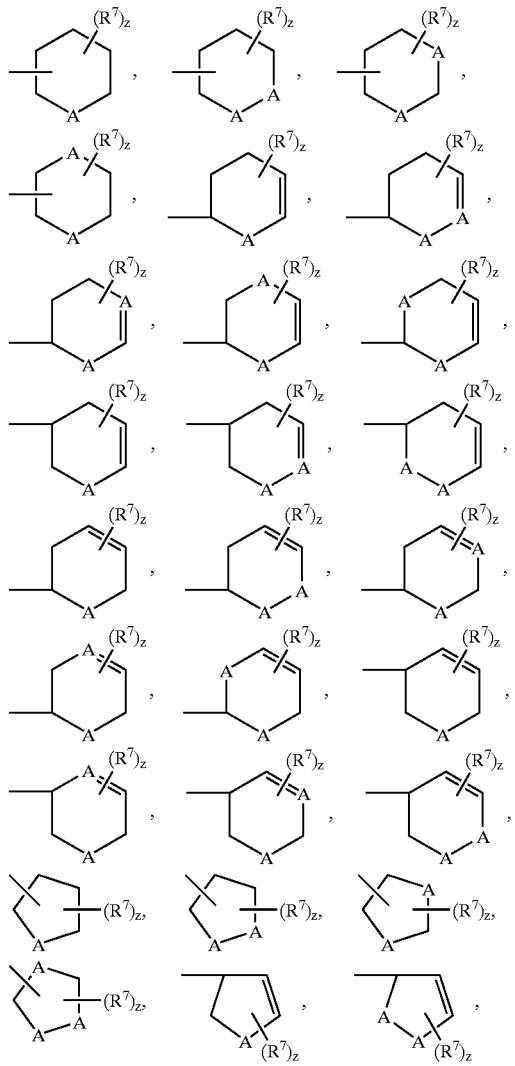

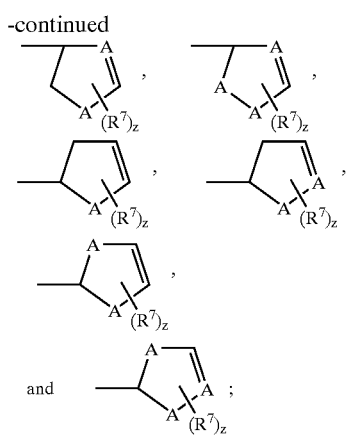

and wherein each R⁷ is independently selected from the group consisting of hydrogen, linear or branched, saturated or unsaturated, substituted or unsubstituted, aliphatic hydrocarbon radical having from about 1 to about 10 carbon atoms, or $R^7$ is a saturated or unsaturated, substituted or unsubstituted, alicyclic or aromatic hydrocarbon or alkoxy radical having, from about 1 to about 10 carbon atoms, which is fused to the heterocyclic ring: each A is independently selected from the group consisting of O, and $N(R^8)_z$, wherein $R_8$ is independently selected from the group consisting of hydrogen, linear or branched, saturated or unsaturated, substituted or unsubstituted, aliphatic hydrocarbon radical having from about 1 to about 10 carbon atoms, and a is either 0 or 1; provided that any A that is bound by a double bond must be $N(R^8)_a$ wherein a=0; z is an integer from 1 to 3.

10. The compound as claimed in claim 9 wherein said heterocycle is selected from the group consisting of:

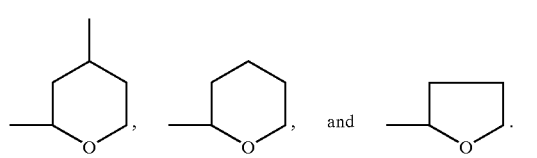

11. The compound as claimed in claim 1 wherein $R^2$ is a 7 to 13 membered substituted, or unsubstituted polycyclic ring.

12. The compound as claimed in claim 1 wherein R is selected from the group consisting of linear or branched, aliphatic hydrocarbon radicals having from about 7 to about 11 carbon atoms; $R_1$ is ethyl; x is a number from 6 to about 10; and $R^2$ is selected from the group consisting of a hydrocarbon radical of the formula

—C(CH₃)₂R³ wherein $R^3$ is selected from the group consisting of linear or branched, aliphatic radicals having from about 3 to about 5 carbon atoms.

13. The compound as claimed in claim 1 wherein $R^2$ is a hydrocarbon of the formula:

—(CH₂)ᵧ—X wherein, y is an integer from 1 to 7; and X is
(a) a 4 to 8 membered substituted, or unsubstituted, partially unsaturated cyclic; hydrocarbon radical;
(b) a 4, 5, 7 or 8 membered substituted or unsubstituted aromatic hydrocarbon radical;
(c) a 6 membered aromatic hydrocarbon radical wherein R is a linear or branched saturated or unsaturated, $C_9$ to $C_{20}$ aliphatic hydrocarbon radical;
(d) an aromatic hydrocarbon selected from the group consisting of:

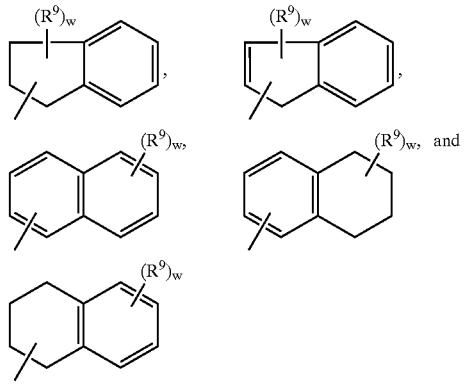

wherein each $R^9$ is independently selected from the group consisting of hydrogen, linear or branched, saturated or unsaturated, substituted or unsubstituted, aliphatic hydrocarbon or alkoxy radical having from about 1 to about 10 carbon atoms; w is an integer from 1 to 3.

14. The compound as claimed in claim 13 wherein X is selected from the group consisting of:

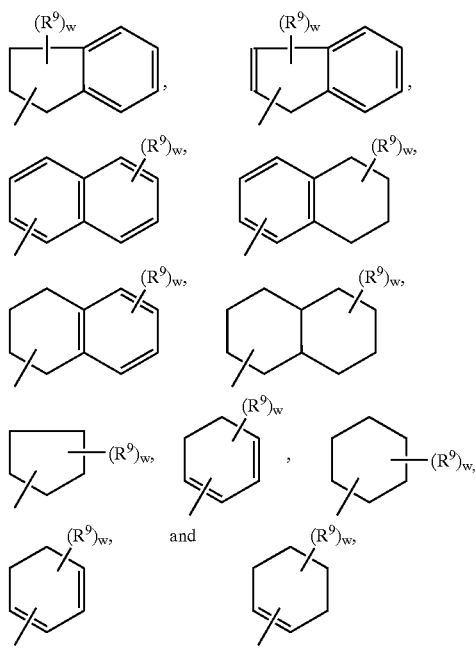

wherein each $R^9$ is independently selected from the group consisting of hydrogen, linear or branched, saturated or unsaturated, substituted or unsubstituted, aliphatic hydrocarbon or alkoxy radical having from about 1 to about 10 carbon atoms; w is an integer from 1 to 3.

15. The compound as claimed in claim 14 wherein X is selected from the group consisting of:

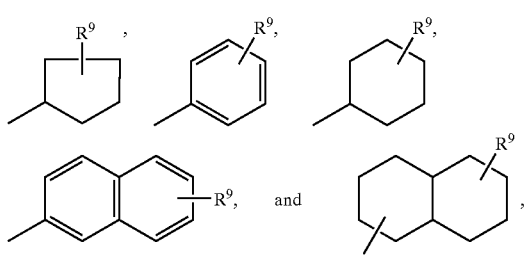

wherein $R^9$ is defined as above.

16. A process for preparing an ether-capped poly(oxyalkylated) alcohol having the formula:

$$RO(R^1O)_xR^2$$

wherein, R is selected from the group consisting of linear or branched, saturated or unsaturated, substituted or unsubstituted, aliphatic or aromatic hydrocarbon radicals having from about 1 to about 30 carbon atoms; $R_1$ may be the same or different, and is independently selected from the group consisting of branched or linear $C_2$ to $C_7$ alkylene in any given molecule; $R^2$ is selected from the group consisting of:
  (a) a 4 to 8 membered substituted, or unsubstituted hetercyclic ring containing from 1 to 3 hetero atoms;
  (b) a 7 to 13 membered substituted or unsubstituted polycyclic ring;
  (c) a hydrocarbon of the formula:

$$-(CH_2)_y-X$$

wherein, y is an integer from 1 to 7, X is selected from the group consisting of:
  (A) a 4 to 8 membered substituted, or unsubstituted, partially unsaturated cyclic hydrocarbon radical;
  (B) a 4, 5, 7 or 8 membered substituted or unsubstituted aromatic hydrocarbon radical;
  (C) a 6 membered aromatic hydrocarbon radical wherein R is a linear or branched saturated or unsaturated, $C_9$ to $C_{20}$ aliphatic hydrocarbon radical;
  (D) an aromatic hydrocarbon selected from the group consisting of:

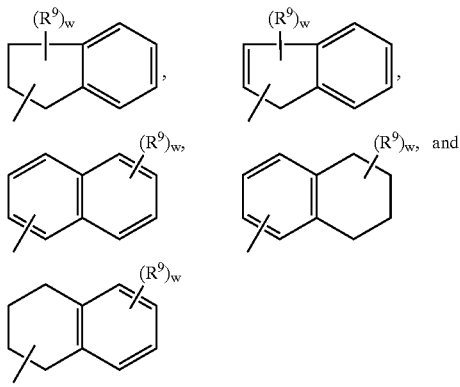

wherein each $R^9$ is independently selected from the group consisting of hydrogen, linear or branched, saturated or unsaturated, substituted or unsubstituted, aliphatic hydrocarbon or alkoxy radical having from about 1 to about 10 carbon atoms; w is an integer from 1 to 3; and (d) a hydrocarbon radical of the formula:

$$-C(CH_3)_2R^3$$

wherein $R^3$ is selected from the group consisting of:
  (A) linear or branched, saturated or unsaturated, aliphatic hydrocarbon radical having from about 2 to about 30 carbon atoms;
  (B) methyl, wherein R is branched saturated or unsaturated aliphatic hydrocarbon radical having from 1 to 4 carbon atoms;
  (C) a substituted or unsubstituted aromatic hydrocarbon radical having from about 15 to about 30 carbon atoms;

wherein x is a number from 1 to about 30; comprising the steps of:
  (a) providing an alcohol of the formula $$R^2OH$$

wherein $R^2$ is as defined above;
  (b) providing an alkoxylated alcohol of the formula $$RO(R^1O)_xH$$

wherein R, $R^1$, and x, are as defined above;
  (c) reacting said alcohol with said alkoxylated alcohol in the presence of a catalyst to form said ether-capped poly(oxyalkylated) alcohol.

17. The process as claimed in claim 16 wherein said catalyst is selected from the group consisting of mineral acids, sulfonic acids and their salts.

18. The process as claimed in claim 16 wherein said catalyst is selected from the group consisting of p-toluenesulfonic acid, methanesulfonic acid, polymeric catalysts, $TiCl_4$, $TiCl_2$, $Ti(OPr)_4$, $ZnCl_2$, $ZnCl_4$, $SnCl_4$, $AlCl_3$, $BF_3$-$OEt_2$, and mixtures thereof.

19. The process as claimed in claim 16 wherein said step of reacting of alcohol with alkoxylated alcohol is conducted in the presence of a solvent wherein said solvent is selected from the group consisting of benzene, toluene, dichloromethane, tetrahydrofuran, diethylether, methyl tert-butylether, and mixtures thereof.

20. The process as claimed in claim 16 wherein said step of reacting alcohol with alkoxylated alcohol is conducted as a temperature of from about −20° C. to about 300° C.

21. The process as claimed in claim 16 wherein said step of reacting alcohol with alkoxylated alcohol is conducted in the absence of a solvent.

22. A process for preparing an ether-capped poly(oxyalkylated) alcohol having the formula:

$$RO(R^1O)_xR^2$$

wherein, R, $R^1$, and x are as defined above; $R^2$ is selected from the group consisting of:
  (a) a 4 to 8 membered substituted, or unsubstituted heterocyclic ring containing from 1 to 3 hetero atoms;
  (b) a 7 to 13 membered substituted, or unsubstituted polycyclic ring;
  (c) a hydrocarbon of the formula:

$$-(CH_2)_y-X$$

wherein, y is an integer from 1 to 7, X is selected from the group consisting of:
  (A) a 4 to 8 membered substituted, or unsubstituted, partially unsaturated cyclic hydrocarbon radical;

(B) a 4, 5, 7 or 8 membered substituted or unsubstituted aromatic hydrocarbon radical;
(C) a 6 membered aromatic hydrocarbon radical wherein R is a linear or branched saturated or unsaturated, $C_9$ to $C_{20}$ aliphatic hydrocarbon radical;
(D) an aromatic hydrocarbon selected from the group consisting of:

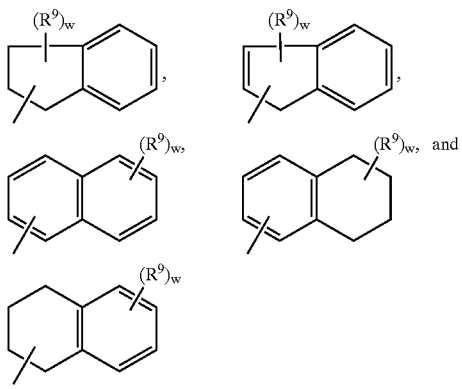

wherein each $R^9$ is independently selected from the group consisting of hydrogen, linear or branched, saturated or unsaturated, substituted or unsubstituted, aliphatic hydrocarbon or alkoxy radical having from about 1 to about 10 carbon atoms; w is an integer from 1 to 3; and
(d) a hydrocarbon radical of the formula:

wherein $R^3$ is selected from the group consisting of:
(A) linear or branched, saturated or unsaturated, aliphatic hydrocarbon radical having from about 2 to a 30 carbon atoms;
(B) methyl, wherein R is branched saturated or unsaturated, aliphatic hydrocarbon radical having from 1 to 4 carbon atoms;
(C) a substituted or unsubstituted aromatic hydrocarbon radical having from about 15 to about 30 carbon atoms;
wherein x is a number from 1 to about 30; comprising the steps of:
(a) providing an alpha-olefin
(b) providing an alkoxylated alcohol of the formula

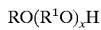

wherein R, $R^1$, and x are as defined above;
(c) reacting said alkoxylated alcohol with said alpha-olefin to form said ether-capped poly(oxyalkylated) alcohol.

23. The process as claimed in claim 22 wherein R is a 4 to 8 member substituted, or unsubstituted heterocyclic ring containing from 1 to 3 hetero atoms.

24. The process as claimed in claim 22 wherein said heterocycle is selected from the group consisting of:

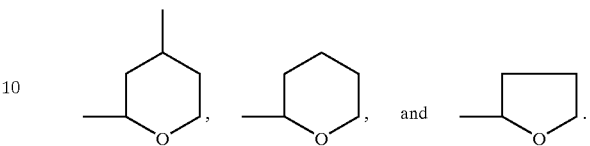

25. The process as claimed in claim 22 wherein said step of reacting of alpha-olefin with alkoxylated alcohol is conducted in the presence of a catalyst.

26. The process as claimed in claim 25 wherein said catalyst is selected from the group consisting of mineral acids, carboxylic acids, sulfonic acids, sulfonic acids, halogenated carboxylic acids, pyridinium p-toluenesulfonate, polymeric catalysts, $TiCl_4$, $Ti(OPr)_4$, $ZnCl_2$, $SnCl_4$, $AlCl_3$, $BF_3$-$OEt_2$, and mixtures thereof.

27. The process as claimed in claim 25 wherein said catalyst is selected from the group consisting of acetic acid, oxalic acid, glycolic acid, citric acid, tartaric acid, glycolic acid, maleic acid oxydisuccinic acid, trifluoroacetic acid, heptaflurobutyric acid, dichloroacetic acid, trichloroacetic acid, p-toluenesulfonic acid, p-toluenesulfinic acid, methanesulfonic acid, 4-bromobenzenesulfonic acid, naphthalenesulfonic acid, (±)-10-camphorsulfonic and isomers, alkylbenzenesulfonic acid, xylenesulfonic acid, cumenesulfonic acid and mixtures thereof.

28. The process as claimed in claim 22 wherein said step of reacting of alpha-olefin with alkoxylated alcohol is conducted in the presence of a solvent, wherein said solvent is selected from the group consisting of benzene, toluene, dichloromethane, tetrahydrofuran, diethylether, methyl tert-butylether, and mixtures thereof.

29. The process as claimed in claim 22 wherein said step of reacting alpha-olefin with alkoxylated alcohol is conducted as a temperature of from about −20° C. to about 300° C.

30. The process as claimed in claim 22 wherein said step of reacting alpha-olefin with alkoxylated alcohol is conducted in the absence of a solvent.

31. A detergent composition comprising an ether-capped poly(oxyalkylated) alcohol according to claim 1.

* * * * *